(12) United States Patent
Atalar et al.

(10) Patent No.: US 6,628,980 B2
(45) Date of Patent: Sep. 30, 2003

(54) APPARATUS, SYSTEMS, AND METHODS FOR IN VIVO MAGNETIC RESONANCE IMAGING

(75) Inventors: Ergin Atalar, Columbia, MD (US); Paul A. Bottomley, Columbia, MD (US); Parag Karmarkar, Elliott City, MD (US); Albert C. Lardo, Baldwin, MD (US); Elias Zerhouni, Pasadena, MD (US)

(73) Assignee: Surgi-Vision, Inc., Chelmsford, MA (US)

( * ) Notice: Subject to any disclaimer, the term of this patent is extended or adjusted under 35 U.S.C. 154(b) by 125 days.

(21) Appl. No.: 09/817,893

(22) Filed: Mar. 26, 2001

(65) Prior Publication Data

US 2002/0045816 A1 Apr. 18, 2002

Related U.S. Application Data

(60) Provisional application No. 60/248,121, filed on Nov. 13, 2000, provisional application No. 60/202,281, filed on May 5, 2000, provisional application No. 60/194,211, filed on Apr. 3, 2000, and provisional application No. 60/192,133, filed on Mar. 24, 2000.

(51) Int. Cl.$^7$ ............................................... A61B 5/055
(52) U.S. Cl. ........................................ 600/423; 324/318
(58) Field of Search ................................ 600/423, 410, 600/411, 425, 426, 429; 324/318, 319, 322

(56) References Cited

U.S. PATENT DOCUMENTS

| | | | |
|---|---|---|---|
| 3,342,175 A | 9/1967 | Bulloch | 128/2 |
| 4,431,005 A | 2/1984 | McCormick | 128/656 |
| 4,445,501 A | 5/1984 | Bresler | 128/1.5 |
| 4,572,198 A | 2/1986 | Codrington | 128/653 |
| 4,643,186 A | 2/1987 | Rosen et al. | 128/303.1 |
| 4,672,972 A | 6/1987 | Berke | 128/653 |
| 4,766,381 A | 8/1988 | Conturo et al. | 324/309 |
| 4,776,341 A | 10/1988 | Bachus et al. | 128/653 |
| 4,791,372 A | 12/1988 | Kirk et al. | 324/318 |
| 4,793,356 A | 12/1988 | Misic et al. | 128/653 |
| 4,813,429 A | 3/1989 | Eshel et al. | 128/736 |
| 4,823,812 A | 4/1989 | Eshel et al. | 128/804 |
| 4,858,613 A | 8/1989 | Fry et al. | 128/660.03 |
| 4,897,604 A | 1/1990 | Carlson et al. | 324/318 |
| 4,922,204 A | 5/1990 | Duerr et al. | 324/322 |

(List continued on next page.)

FOREIGN PATENT DOCUMENTS

| | | | |
|---|---|---|---|
| EP | 0 659 385 A1 | 6/1995 | |
| EP | 0 673 621 A1 | 9/1995 | |
| EP | 0 768 539 A2 | 4/1997 | |
| EP | 0 850 595 A1 | 7/1998 | |
| EP | 0 908 739 A2 | 4/1999 | |
| JP | 6-70902 | 3/1994 | |
| JP | 7-299046 A | * 11/1995 | A61B/5/055 |
| WO | WO 98/52064 | 11/1998 | |
| WO | WO 98/52461 | 11/1998 | |
| WO | WO 99/18852 | 4/1999 | |
| WO | WO 99/27390 | 6/1999 | |
| WO | WO 99/59479 | 11/1999 | |
| WO | WO 00/64003 | 10/2000 | |

OTHER PUBLICATIONS

Lardo, A.C.; "Real–Time Magnetic Resonance Imaging: Diagnostic and Interventional Applications", Pediatric Cardiology, Springer–Verlag, NY, US., vol. 21, No. 1: 80–98, (Jan. 2000).

(List continued on next page.)

*Primary Examiner*—Hieu Vo
(74) *Attorney, Agent, or Firm*—Foley Hoag LLP

(57) ABSTRACT

The apparatus, systems and methods of the present invention provide for MRI sleeves, probes, and combinations thereof adapted for insertion into a subject, in order to internally image regions of the subject.

51 Claims, 15 Drawing Sheets

U.S. PATENT DOCUMENTS

| | | | |
|---|---|---|---|
| 4,932,411 A | 6/1990 | Fritschy et al. | 128/653 |
| 4,960,106 A | 10/1990 | Kubokawa et al. | 128/6 |
| 5,019,075 A | 5/1991 | Spears et al. | 606/7 |
| 5,035,231 A | 7/1991 | Kubokawa et al. | 128/6 |
| 5,050,607 A | 9/1991 | Bradley et al. | 128/653 A |
| 5,090,959 A | 2/1992 | Samson et al. | 604/96 |
| 5,095,911 A | 3/1992 | Pomeranz | 128/662.06 |
| 5,099,208 A | 3/1992 | Fitzpatrick et al. | 324/312 |
| 5,167,233 A | 12/1992 | Eberle et al. | 128/662.06 |
| 5,170,789 A | 12/1992 | Narayan et al. | 128/653.5 |
| 5,190,046 A | 3/1993 | Shturman | 128/662.06 |
| 5,211,165 A | 5/1993 | Dumoulin et al. | 128/653.1 |
| 5,211,166 A | 5/1993 | Sepponen | 128/653.5 |
| 5,217,010 A | 6/1993 | Tsitlik et al. | 128/419 P |
| 5,260,658 A | 11/1993 | Greim et al. | 324/322 |
| 5,270,485 A | 12/1993 | Jacobsen | 174/15.1 |
| 5,271,400 A | 12/1993 | Dumoulin et al. | 128/653.2 |
| 5,293,872 A | 3/1994 | Alfano et al. | 128/664 |
| 5,294,886 A | 3/1994 | Duerr | 324/318 |
| 5,307,808 A | 5/1994 | Dumoulin et al. | 128/653.2 |
| 5,307,814 A | 5/1994 | Kressel et al. | 128/653.5 |
| 5,318,025 A | 6/1994 | Dumoulin et al. | 128/653.2 |
| 5,323,778 A * | 6/1994 | Kandarpa et al. | 600/411 |
| 5,348,010 A | 9/1994 | Schnall et al. | 128/653.2 |
| 5,352,979 A | 10/1994 | Conturo | 324/307 |
| 5,355,087 A | 10/1994 | Claiborne et al. | 324/322 |
| 5,358,515 A | 10/1994 | Hürter et al. | 607/101 |
| 5,365,928 A | 11/1994 | Rhinehart et al. | 128/653.5 |
| 5,370,644 A | 12/1994 | Langberg | 606/33 |
| 5,372,138 A | 12/1994 | Crowley et al. | 128/662.06 |
| 5,375,596 A | 12/1994 | Twiss et al. | 128/653.1 |
| 5,400,787 A | 3/1995 | Marandos | 128/653.5 |
| 5,411,476 A | 5/1995 | Abrams et al. | 604/95 |
| 5,413,104 A | 5/1995 | Buijs et al. | 1128/653.5 |
| 5,419,325 A | 5/1995 | Dumoulin et al. | 128/653.2 |
| 5,421,338 A | 6/1995 | Crowley et al. | 128/662.06 |
| 5,429,132 A | 7/1995 | Guy et al. | 128/653.1 |
| 5,435,302 A | 7/1995 | Lenkinski et al. | 600/422 |
| 5,437,277 A | 8/1995 | Dumoulin et al. | 128/653.1 |
| 5,439,000 A | 8/1995 | Gunderson et al. | 128/664 |
| 5,443,066 A | 8/1995 | Dumoulin et al. | 128/653.1 |
| 5,443,489 A | 8/1995 | Ben-Haim | 607/115 |
| 5,447,156 A | 9/1995 | Dumoulin et al. | 128/653.2 |
| 5,451,232 A | 9/1995 | Rhinehart et al. | 606/192 |
| 5,451,774 A | 9/1995 | Jacobsen | 250/227.24 |
| 5,462,055 A | 10/1995 | Casey et al. | 128/653.5 |
| 5,476,095 A | 12/1995 | Schnall et al. | 128/653.2 |
| 5,498,261 A | 3/1996 | Strul | 606/29 |
| 5,507,743 A | 4/1996 | Edwards et al. | 606/41 |
| 5,512,825 A | 4/1996 | Atalar et al. | 324/309 |
| 5,520,644 A | 5/1996 | Imran | 604/95 |
| 5,524,630 A | 6/1996 | Crowley | 128/662.06 |
| 5,540,679 A | 7/1996 | Fram et al. | 606/27 |
| 5,558,093 A | 9/1996 | Pomeranz | 128/660.03 |
| 5,572,132 A * | 11/1996 | Pulyer et al. | 324/318 |
| 5,578,008 A | 11/1996 | Hara | 604/94 |
| 5,588,432 A | 12/1996 | Crowley | 128/660.03 |
| 5,598,097 A | 1/1997 | Scholes et al. | 324/316 |
| 5,609,606 A | 3/1997 | O'Boyle | 606/194 |
| 5,611,807 A | 3/1997 | O'Boyle | 606/169 |
| 5,623,241 A | 4/1997 | Minkoff | 335/296 |
| 5,647,361 A | 7/1997 | Damadian | 128/683.2 |
| 5,660,180 A | 8/1997 | Malinowski et al. | 128/660.03 |
| 5,682,897 A | 11/1997 | Pomeranz | 128/662.06 |
| 5,699,801 A | 12/1997 | Atalar et al. | 128/653.2 |
| 5,715,825 A | 2/1998 | Crowley | 128/602.06 |
| 5,728,079 A | 3/1998 | Weber et al. | 604/280 |
| 5,738,632 A | 4/1998 | Karasawa | 600/410 |
| 5,775,338 A | 7/1998 | Hastings | 128/898 |
| 5,792,055 A | 8/1998 | McKinnon | 600/410 |
| 5,833,632 A | 11/1998 | Jacobsen et al. | 600/585 |
| 5,840,031 A | 11/1998 | Crowley | 600/440 |
| 5,868,674 A | 2/1999 | Glowinski et al. | 600/410 |
| 5,916,162 A | 6/1999 | Snelten et al. | 600/411 |
| 5,928,145 A | 7/1999 | Ocali et al. | 600/410 |
| 5,938,609 A | 8/1999 | Pomeranz | 600/439 |
| 5,938,692 A | 8/1999 | Rudie | 607/101 |
| 5,964,705 A | 10/1999 | Truwit et al. | 600/423 |
| 5,968,052 A | 10/1999 | Sullivan, III et al. | 606/108 |
| 6,004,269 A | 12/1999 | Crowley et al. | 600/439 |
| 6,011,995 A | 1/2000 | Guglielmi et al. | 607/99 |
| 6,171,240 B1 | 1/2000 | Young et al. | 600/410 |
| 6,019,737 A | 2/2000 | Murata | 600/585 |
| 6,026,316 A | 2/2000 | Kucharczyk et al. | 600/420 |
| 6,031,375 A | 2/2000 | Atalar et al. | 324/307 |
| 6,032,078 A | 2/2000 | Rudie | 607/101 |
| 6,051,974 A | 4/2000 | Reisker et al. | 324/318 |
| 6,058,323 A | 5/2000 | Lemelson | 600/408 |
| 6,061,587 A | 5/2000 | Kurcharczyk et al. | 600/411 |
| 6,078,831 A | 6/2000 | Belef et al. | 600/424 |
| 6,104,943 A | 8/2000 | Frederick et al. | 600/410 |
| 6,216,044 B1 | 4/2001 | Kordis | 607/122 |
| 6,437,569 B1 * | 8/2002 | Minkoff et al. | 324/318 |
| 2001/0056232 A1 * | 12/2001 | Lardo et al. | 600/423 |

OTHER PUBLICATIONS

Atalar et al.; "High Resolution Intravascular MRI and MRS using a Catheter Receiver Coil,", Magnetic Resonance in Medicine, 36:595–605 (1996).

Edelman et al.; "Magnetic Resonance Imaging" NEJM. 328: 708–716 (1993).

Farmer et al.;"Implanted Coil MR Microscopy of RenalPathology", Magn. Reson. Med., 10: 310–323 (1989).

Garwood et al.; "Magnetic Resonance Imaging with Adiabatic Using a Single Surface Coil for RF Transmission and Signal Detection", Magnetic Resonance in Medicine 9: 25–34 (1989).

Hoult et al.; "Signal–to–Noise Ratio of the Nuclear Magnetic Resonance Experiment" J. Magn. Reson. ,24: 71–85 (1976).

Hoult; "Rotating Frame Zeugmatography", Phil. Trans. R. Soc. Lond. B. 289:543–547 (1980).

Jolesz et al. ; "Interventional Magnetic Resonance Therapy", Seminars in Interventional Radiology , 12: 20–27 (1995).

Ladd et al.; "Guidewire Antennas for MR Fluoroscopy", Magnetic Resonance in Medicine, Academic Press, Duluth, MN, US., vol. 37(6): 891–897, (Jun. 1, 1997).

Martin et al.; "An Expandable Intravenous RF Coil for Imaging the Artery Wall", Proceeding of the International Society for Magnetic Resonance in Medicine, Fourth Scientific Meeting and Exhibition, New York, USA Apr. 27–May 3, 1996, vol. 1, p. 402.

Ocali et al.; "Intravascular Magnetic Resonance Imaging Using a Loopless Catheter Antenna", MRM, 37: 112–118 (1997).

Quick et al; "Vascular Stents as RF–Antennas for Intravascular MR–Guidance and–Imaging", Proceedings of the International Society for Magnetic Resonance in Medicinek, Seventh Scientific Meeting and Exhibition, Philadelphia, Pennsylvania, USA May 22–28 1999, vol. 1, p. 577.

Silverman et al; "Interactive MR–guided Biopsy in an Open configuration MR Imaging System", Radiology, 197: 175–181 (1995).

International Search Report Completed on Oct. 12, 2001 and Mailed on Nov. 08, 2001.

* cited by examiner

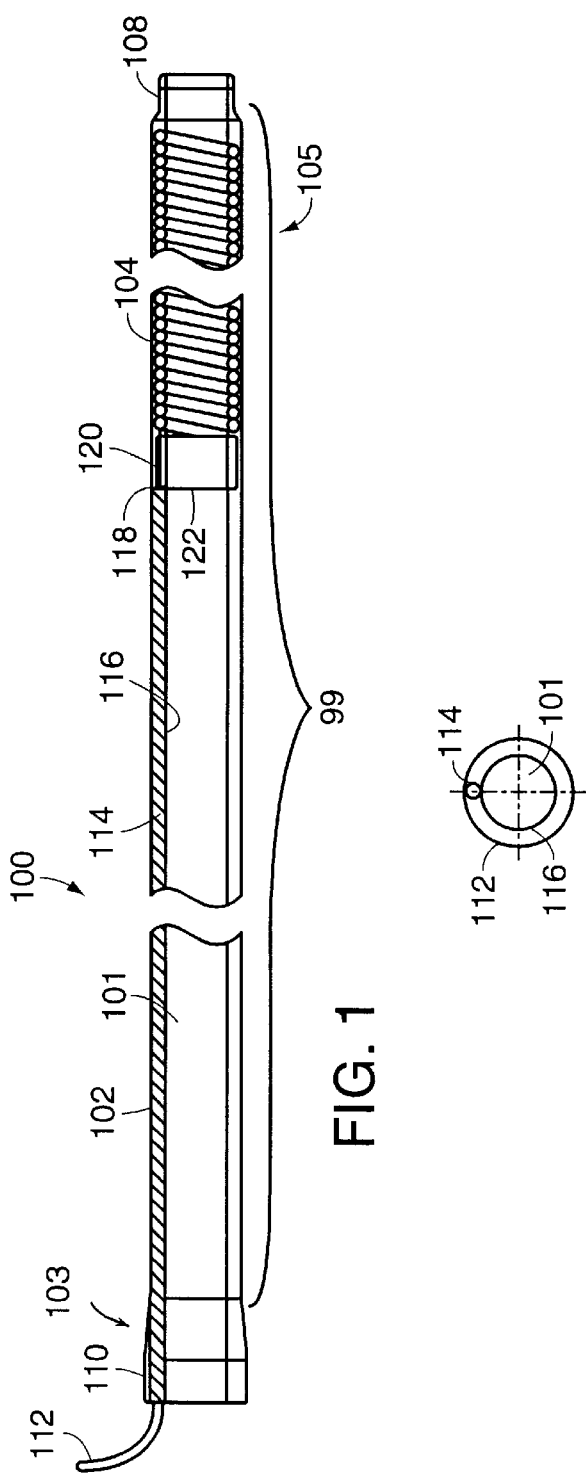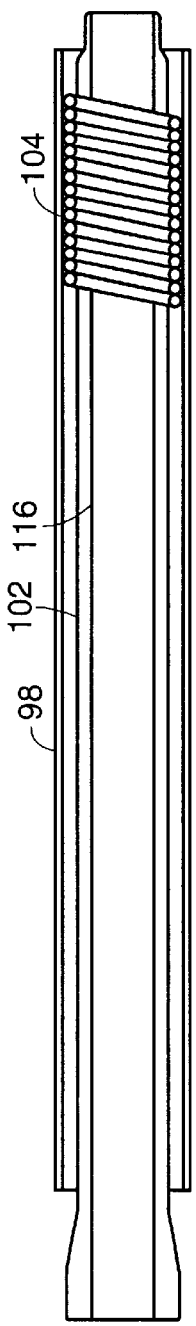

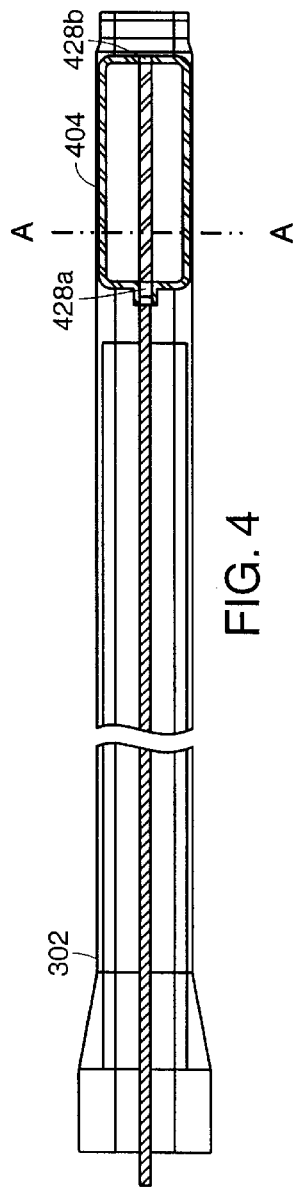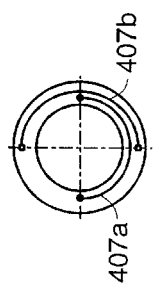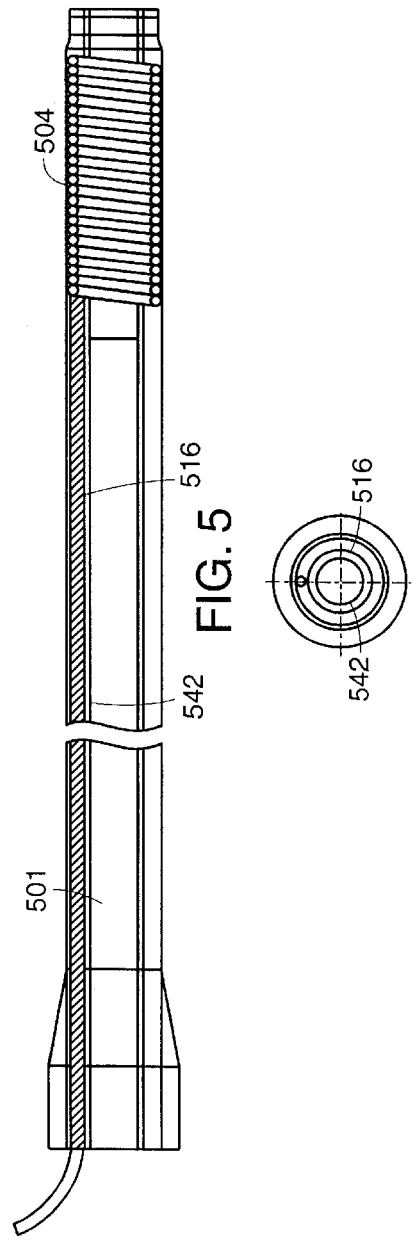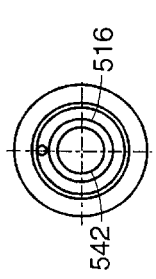

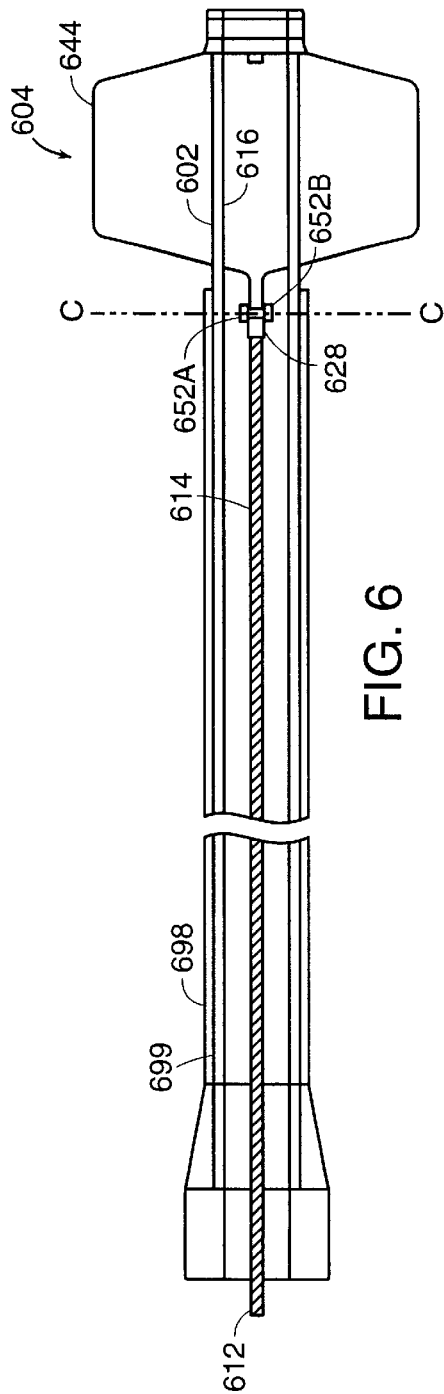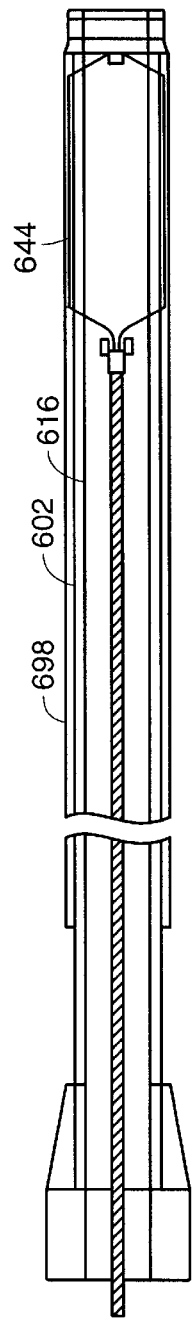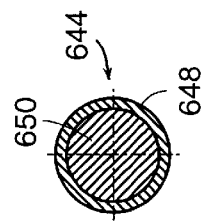
FIG. 6
FIG. 6A
FIG. 6B

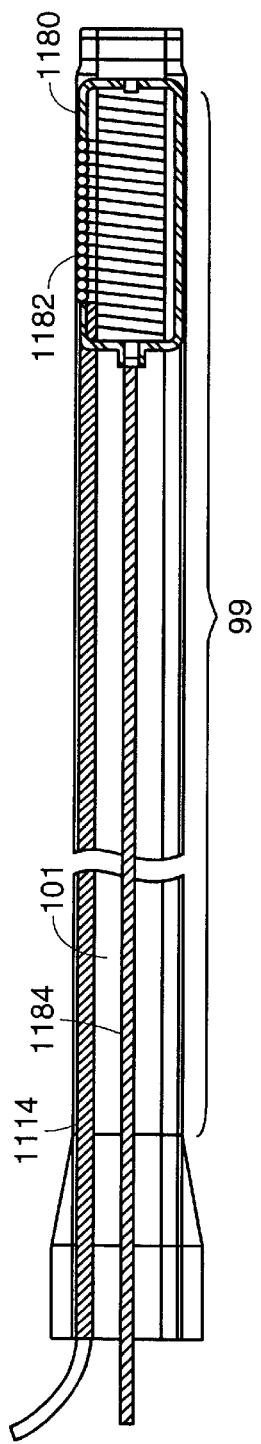
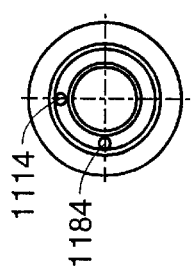
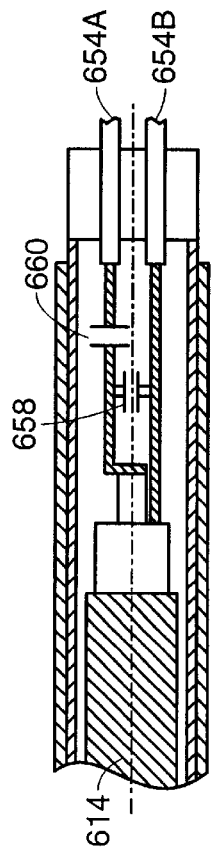
FIG. 11
FIG. 11A
FIG. 12

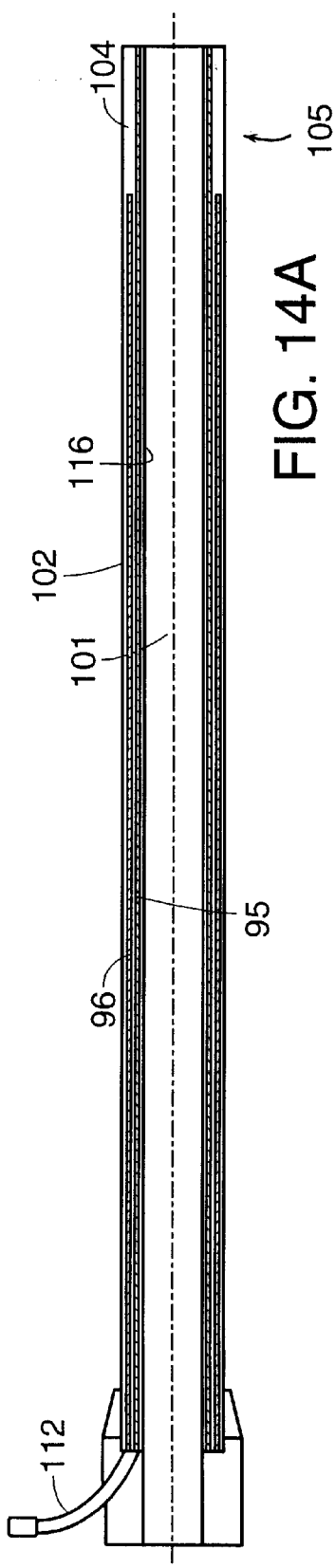
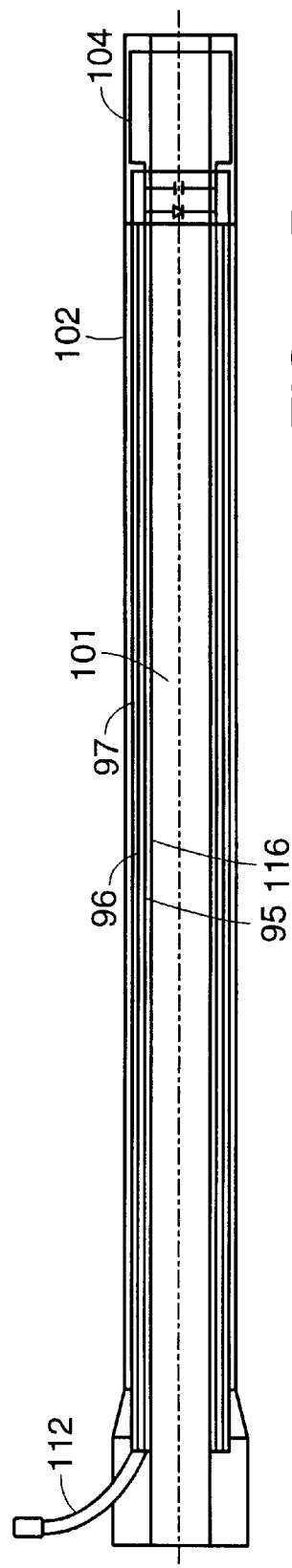

APPARATUS, SYSTEMS, AND METHODS FOR IN VIVO MAGNETIC RESONANCE IMAGING

REFERENCE TO RELATED APPLICATIONS

This application claims the benefit of U.S. Provisional Patent Application No. 60/192,133 filed Mar. 24, 2000, U.S. Provisional Patent Application No. 60/194,211, filed Apr. 3, 2000, U.S. Provisional Patent Application No. 60/202,281, filed May 5, 2000, and U.S. Provisional Patent Application No. 60/248,121, filed Nov. 13, 2000. The entire disclosure of all of these applications is herein incorporated by reference.

BACKGROUND OF THE INVENTION

1. Field of the Invention

The invention relates in general to magnetic resonance imaging (MRI), and in particular to devices for in vivo MRI.

2. Related Art

Minimally invasive surgical techniques often involve introducing a medical device e.g. an endoscope in any body lumen (natural or man-made) to provide an optical view of anatomy of interest. Surgical tools such as biopsy needles, incision/suturing devices, etc are used under optical guidance of the endoscope. The limitation of this technique is that the field of view (FOV) is limited in front of the device, in some cases by the end of the cavity. In particular, nothing can be seen beyond the surface of the tissue surrounding the endoscope. This poses a limitation for the operating surgeon, limiting the efficacy of the procedure. One approach to circumvent this problem is to employ imaging systems relying on signals other than visible light to generate an image of surrounding tissue. One such system is magnetic resonance imaging (MRI).

MRI is a well known, highly useful technique for imaging matter. It has particular use with imaging the human body or other biological tissue without invasive procedures or exposure to the harmful radiation or chemicals present with x-rays or CT scans. MRI uses changes in the angular momentum or "spin" of atomic nuclei of certain elements to show locations of those elements within matter. In an MRI procedure, a subject is usually inserted into an imaging machine that contains a large static magnetic field generally on the order of 0.2 to 4 Tesla although machines with higher and lower strength fields are being developed and used. This static magnetic field tends to cause the vector of the magnetization of the atomic nuclei placed therein to align with the magnetic field. The subject is then exposed to pulses of radio frequency (RF) energy in the form of a second, oscillating, RF magnetic field having a particular frequency referred to in the art as a resonant or Larmor frequency. This frequency is equal to the rate that the spins rotate or precess.

This second field is generally oriented so that its magnetic field is oriented in the transverse plane to that of the static magnetic field and is generally significantly smaller. The second field pulls the net magnetism of the atomic nuclei off the axis of the original magnetic field. As the second magnetic field pulses, it pulls the spins off axis. When it is turned off, the spins "relax" back to their position relative to the initial magnetic field. The rate at which the spins relax is dependent on the molecular level environment. During the relaxation step, the precessing magnetization at the Larmor frequency induces a signal voltage that can be detected by antennas tuned to that frequency. The magnetic resonance signal persists for the time it takes for the spins to relax. Since different tissues have different molecular level environments, the differences in relaxation times provides a mechanism for tissue contrast in MRI. The magnetic resonance signal is detected in the form of a voltage that the precessing magnetization induces in an antenna placed nearby.

In order to image the magnetic resonance signal it is necessary to encode the locations of the resonant spins. This is performed by applying pulses of gradient magnetic fields to the main magnetic field in each of the three dimensions. By creating these fields, the location of resonant nuclei can be determined because the nuclei will resonate at a different Larmor frequencies since the magnetic field they experience differs from their neighbors. The magnetic resonance (MR) image is a representation of the magnetic resonance signal on a display in two or three dimensions. This display usually comprises slices taken on an axis of interest in the subject, or slices in any dimension or combination of dimensions, three-dimensional renderings including computer generated three-dimensional "blow-ups" of two-dimensional slices, or any combination of the previous, but can comprise any display known to the art.

MR signals are very weak and therefore the antenna's ability to detect them depends on both its size and its proximity to the source of those signals. In order to improve the signal of an MRI, the antenna may be placed near or inside the subject to be imaged. Such improvements can enable valuable increases in resolution sensitivity and reduction of scan time. It may be desirable to have evidence of the MRI antenna itself on the MRI image to allow the individual inserting the MRI antenna to direct where it is going and to maneuver it with aid from the MR image. Such a benefit could be useful in medical procedures where MRI is used simultaneously to track the position of an intraluminal device and to evaluate the structures surrounding the lumen. For example, an intravascular catheter could be directed through a vessel using MRI to reach a targeted area of the vessel, and the MRI apparatus could further be used to delineate the intravascular anatomy or nearby tissue to determine whether a particular therapeutic intervention would be required. Using MRI to guide the catheter and using MRI further to map out the relevant anatomy could complement conventional angiographic imaging technology within an interventional radiology or cardiology or minimally invasive imaging suite. Once the catheter is directed to the desired anatomic target under MR guidance, and once the topography or other relevant anatomy of the target lesion is depicted using MRI, the clinician can make decisions about what type of intervention would be indicated, if any, and where the intervention should be delivered.

Many conventional vascular interventional procedures use X-ray imaging technology in which guidewires and catheters are inserted into a vein or artery and navigated to specific locations in the heart for diagnostic and therapeutic procedures. Conventional X-ray guided vascular interventions, however, suffer from a number of limitations, including: (1) limited anatomical visualization of the body and blood vessels during the examination, (2) limited ability to obtain a cross-sectional view of the target vessel, (3) inability to characterize important pathologic features of atherosclerotic plaques, (4) limited ability to obtain functional information on the state of the related organ, and (5) exposure of the subject to potentially damaging x-ray radiation.

MRI techniques offer the potential to overcome these deficiencies. However, many conventional intraluminal tools are not suitable for use in MRI machines since they contain steel or magnetic materials that can cause significant image artifacts in an MRI machine and can cause injury to a patient from unintended motion due to effects of the magnetic fields or induced Ohmic heating. Additionally, intraluminal devices made of non-magnetic materials (e.g., polymers) cannot easily be visualized by MRI. Even those antennae which have been fabricated for use inside a human body are not useful for many types of interventional procedures. Many of these devices are simply too large to be sufficiently miniaturized to allow the placement of an interventional device simultaneously with the antenna in a small vessel without causing injury to the subject. Furthermore, many of these devices are not useful because the antenna cannot work in conjunction with the range of interventional tools that are widely used in many types of procedures due to space and design considerations of the antenna. Such devices include, but are not limited to, such tools as balloon catheters for dilatation angioplasties, for stent placements, for drug infusions, and for local vessel therapies such as gene therapies; atherotomes and other devices for plaque resection and debulking; stent placement catheters; drug delivery catheters; intraluminal resecting tools; electrophysiologic mapping instruments; lasers and radio frequency and other ablative instruments. Conventional antennas fail in this regard because they have no method for allowing the loading and use of these devices concurrent with image acquisition by the antenna.

Various imaging coils for interventional MRI are known in the art. U.S. Pat. No. 5,738,632 to Karasawa, discloses an endoscope/rigidoscope with MRI coils located in the distal section of the device. U.S. Pat. No. 5,699,801 to Atalar et al (hereafter "Atalar '801") describes a loop antenna for interventional MRI and spectroscopy applications. The distance between the two sides of the loop is fixed and is approximately 2–3 mm. This separation is relatively small, which results in a received signal having a lower signal-to-noise ratio (SNR) than could be achieved with a larger separation. The caliber of such a device is limited, however, by the size of the smallest bodily structure through which it might be advanced. For example, if device according to Atalar '801 were to be advanced through a vein with a diameter of 5 mm into a second vein with a diameter of 15 mm and finally into a heart chamber with a diameter to 40 mm, the device, its coil, and any other parts must all be less than 5 mm in caliber. If a device with a caliber of, for example, 25 mm were practiced according to Atalar '801, it could not be used in the preceding example because its size is fixed, and it could not fit through the smallest structure in the desired path of the device.

In applications of such MRI coils, it would be desirable to introduce adjacent to the MRI antenna other devices including PTCA catheters, endoscopes, trocars, other minimally invasive surgical equipment or MRI antennae for the purpose of diagnosis or therapeutic intervention. The prior art does not provide for such a capability.

Also in applications of such MRI coils, it is desirable to introduce the MRI antenna into a cavity, access to which is available only through very narrow lumens. For example, access to chambers of the heart is limited by the caliber of blood vessels entering and exiting the heart. Thus, a low profile device is needed to gain access to such cavities. This necessity introduces all the limitations of existing low profile devices, primarily diminished SNR. In addition, if the narrow-lumen access pathway is a vascular structure, a device completely occluding that lumen might not be usable in that lumen since tissues whose blood supply depends on the patency of that vessel would be starved of oxygen. The prior art does not provide a means for an MRI antenna to make use of additional available space once the antenna has been fully advanced into a cavity with a lumen larger than its access structures, or for positioning an MRI antenna in a structure while leaving that structure at least partly patent throughout its length.

Catheters have long been used in the art as sleeves through which other medical devices may be advanced to an anatomical point of interest for examination, diagnosis, and intervention. However, advancement of the catheter requires constant monitoring to ensure that the catheter is being advanced through the correct structures, without kinking, causing injury, failing mechanically, and for other reasons known to one skilled in the art. Methods existing in the art for such monitoring include X-ray visualization of the catheter, and MRI tracing of a component of the catheter designed to be visible to an MRI antenna. These methods are of limited usefulness because, in the case of the X-ray method, the subject and the persons operating the device are exposed to potentially harmful X-rays. In the case of MRI tracing, the catheter cannot be used for imaging but only for catheter location. Therefore if an unexpected obstruction is encountered by the individual threading the catheter, additional interventional tools or imaging techniques must be used. This can result in increased possibility of injury for a patient, and increased difficulty of the procedure.

U.S. Pat. No. 5,348,010 to Schnall et al. discloses an inflatable MRI receiver coil employing a balloon. The tuning matching components in the Schnall device are placed outside the patient, thereby reducing the SNR of the received signal. Further, the balloon must be inflated during image acquisition, thereby occluding the entire diameter of the vessel in which it is placed, limiting or precluding its use in vascular applications where blood flow is desired during image acquisition, or, for extended periods of time, the airways. The distance between the receiver coil conductors in the Schnall device is also not fixed at any point along its inflation, which limits the tuning matching and decoupling components as they cannot be predetermined for a loop of a particular size while imaging.

There remains a need in the art for an MRI imaging device sleeve incorporating a flexible elongated MRI antenna suitable for a wide variety of interventional applications.

SUMMARY

In accordance with the embodiments of the invention, systems and methods are provided herein for imaging using magnetic resonance imaging.

As used herein, the following terms generally encompass the following meanings, although these definitions do not limit the meaning of these words as would be understood by one of skill in the art.

"Internally imaging" generally denotes the acquisition of data interpretable as an image from an antenna situated within the confines of a structure to be imaged or within a body containing the structure to be imaged.

"Adjacent" generally denotes the condition of being inside of, next to, or in proximity of an object of reference. It may also denote the condition of being within the same body that contains the object of reference.

"Detector coil," "imaging coil," and "coil" are synonymous terms that generally denote any arrangement of an electrically conductive and magnetic resonance compatible material acting as an antenna to receive and convey magnetic resonance data.

"Sleeve" generally denotes an object which surrounds a lumen or may be considered hollow by one of ordinary skill in the art. It may be of any shape. However, a sleeve will often refer to a tubular shape herein.

"Imaging sleeve" generally denotes a sleeve attached to a detector coil for internally imaging.

"MRI sleeve" generally denotes an imaging sleeve dimensionally and/or constitutionally adapted for use in magnetic resonance imaging.

"Dimensionally different" generally denotes the condition in which one state of an object of reference differs from another state by the shape of the volume of space occupied by the object.

"Probe" generally denotes any object that is adapted for passage through a substantially tubular member.

Certain embodiments comprise an apparatus for internally imaging using magnetic resonance imaging, having a first substantially tubular member including a distal and a proximal end and an interior and exterior surface, and a detector coil attached to the tubular member for internally imaging using MRI. In an embodiment, the detector coil is attached in proximity to the distal end of the tubular member. In another embodiment, the detector coil is located on the exterior surface.

In yet another embodiment, the detector coil is embedded within the tubular member. In another embodiment, the apparatus further comprises an electrical transmission member for electrically connecting the detector coil to an MRI scanner. In an embodiment, the electrical transmission member is located on the exterior surface of the first tubular member. In an embodiment, the electrical transmission member is a coaxial cable. In an embodiment, the electrical transmission member is a triaxial cable.

In one embodiment, the apparatus further comprises a second substantially tubular member placed coaxially with the first substantially tubular member. In an embodiment, the second tubular member is slideably related to the first tubular member.

In an embodiment, the detector coil includes at least one of a loop coil, a quadrature loop coil, a loopless coil, a loop expandable coil, a quadrature loop expandable coil, or a loopless expandable coil. In an embodiment, the first tubular member is dimensionally adapted for insertion into a body. In an embodiment, the first tubular member is dimensionally adapted for passage of medical devices therein.

In an embodiment, the detector coil resides on a flexible circuit board. In an embodiment, the detector coil comprises a solenoid.

In an embodiment, the apparatus further comprises a probe. In an embodiment, the probe includes a probe detector coil. In an embodiment, the probe detector coil includes at least one of a loop coil, a quadrature loop coil, a loopless coil, a loop expandable coil, a quadrature loop expandable coil, or a loopless expandable coil.

In an embodiment, the apparatus further comprises an attachment point disposed at the distal end of the first tubular member to affix the tubular member to an attached device. In an embodiment, the attached device includes a medical device. In an embodiment, the attached device is permanently affixed to the first tubular member. In an embodiment, the attached device is temporarily attached to the first tubular member. In an embodiment, the apparatus may further comprise a connector hub disposed at the proximal end of the first tubular member. In an embodiment, the connector hub includes strain relief.

In an embodiment, the apparatus further comprises an interface system having a tuning/matching circuit and a decoupling circuit, and is interposed between the detector coil and an MRI imaging system.

In an embodiment, the exterior surface and interior surface are coated with a lubricious material. In an embodiment, the lubricious material includes at least one of polyvinylpyrrolidone, polyacrylic acid, or silicone.

An embodiment comprises an apparatus for imaging using magnetic resonance imaging (MRI) including a substantially tubular member having a distal end, a proximal end, and a lumen extending between said distal and said proximal end, and a detector coil for imaging, using magnetic resonance imaging (MRI), wherein the tubular member is moveable between at least two states relative to the detector coil, such that in the first state the detector coil is positioned within the lumen and in the second state the detector coil is extended beyond the lumen to permit imaging.

In an embodiment, the detector coil includes at least one of a loop expandable coil, a quadrature loop expandable coil, or a loopless expandable coil. In an embodiment, the detector coil in the second state is expanded. In an embodiment, the detector coil in the first state is dimensionally different from the detector coil in the second state. In an embodiment, the detector coil is placed in a subject in the first state and detects magnetic resonance in the subject in the second state. In an embodiment, the detector coil is dimensionally adapted for insertion into and advancement through a catheter. In an embodiment, the detector coil can image in the first state.

In certain embodiments, the apparatus may further comprise a body lumen obstruction device. In an embodiment, the apparatus may further comprise an interface system having a tuning/matching circuit and a decoupling circuit, and the interface system is interposed between the detector coil and an MRI imaging system.

Another embodiment provides a method for imaging using magnetic resonance imaging comprising placing a first and a second detector coil internal to a subject and adjacent to an area for imaging, generating magnetic resonance in the area, and moving the first detector coil relative to the second detector coil so that the coils in combination detect the magnetic resonance.

In an embodiment, wherein the step of placing, at least one of the first detector coil and the second detector coil can detect the magnetic resonance. In an embodiment, wherein the step of placing, magnetic resonance is generated.

Another embodiment provides a system for imaging using magnetic resonance imaging, comprising a first detector coil for internally detecting magnetic resonance, a second detector coil for internally detecting magnetic resonance, and a controller for using the first detector coil in combination with the second detector coil for detecting magnetic resonance in an area to be imaged.

Another embodiment provides a system for imaging using magnetic resonance imaging, comprising means for placing a first and a second detector coil internal to a subject and adjacent to an area for imaging, and means for moving the first detector coil relative to the second detector coil so that the coils in combination detect magnetic resonance.

Another embodiment provides an apparatus for internally imaging using MRI, comprising a detector coil for internally imaging using MRI, and a trigger mechanism in communication with the detector coil, wherein activation of the trigger mechanism causes the detector coil to change from a collapsed state to an expanded state. In an embodiment, the trigger mechanism comprises a pull wire. In an embodiment, the detector coil in the collapsed state is dimensionally different from the detector coil in the expanded state.

BRIEF DESCRIPTION OF THE DRAWINGS

The foregoing and other embodiments, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

FIG. 1 shows a cross-sectional view illustrating an imaging sleeve according to a first embodiment having a loopless imaging antenna.

FIG. 1A shows a proximal end view of the embodiment depicted in FIG. 1.

FIG. 1B shows a cross-sectional view illustrating an embodiment having two tubular members.

FIG. 4 shows a cross-sectional view illustrating an imaging sleeve according to an embodiment having a quadrature loop imaging coil.

FIG. 4A shows a cut-section view of the embodiment depicted in FIG. 4 taken through the line A—A indicated in FIG. 4.

FIG. 5 shows a cross-sectional view illustrating an imaging sleeve according to an embodiment adapted for use with a second medical device.

FIG. 5A shows a proximal end view of the embodiment depicted in FIG. 5.

FIG. 6 shows a cross-sectional view illustrating an imaging sleeve according to an embodiment having an expandable loop imaging coil with the expandable loop imaging coil in its expanded state.

FIG. 6A shows a cross-sectional view illustrating an imaging sleeve according to an embodiment having an expandable loop imaging coil with the expandable loop imaging coil in its collapsed state.

FIG. 6B shows a cross-sectional view of the imaging loop coil of FIG. 6.

FIG. 11 shows a cross-sectional view illustrating an MRI sleeve according to an embodiment having a loop imaging coil and a loopless imaging coil embedded in the sleeve.

FIG. 11A shows a left-end cross-sectional view of the embodiment depicted in FIG. 11.

FIG. 12 shows a cross-sectional view illustrating an arrangement of the capacitors of a tuning/mating circuit of the invention according to an embodiment having a loop imaging coil.

FIG. 14A shows a cross-section view illustrating an imaging sleeve.

FIG. 14B shows a cross-section view illustrating an imaging sleeve.

DETAILED DESCRIPTION

Figure 2:
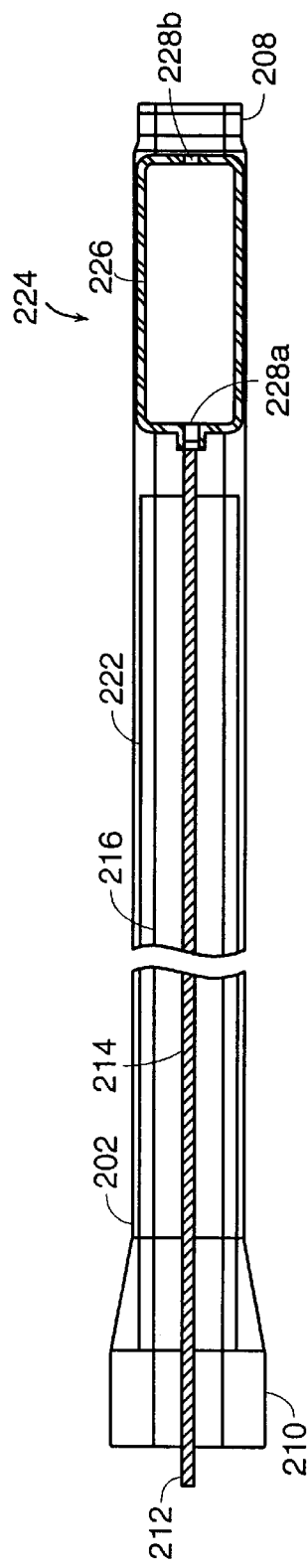
FIG. 2 shows a cross-sectional view illustrating an imaging sleeve according to a second embodiment having a loop antenna imaging coil.

The invention will now be described with reference to certain illustrated embodiments and certain exemplary practices. However, it should be understood that the following description is only meant to be illustrative of the invention and is not meant to limit the scope of the invention which is applicable to other forms of anatomic evaluation, diagnosis and treatment, as will be evident to practitioners in the art. The below described embodiments primarily refer to the use of apparatuses for imaging internally to a structure using magnetic resonance imaging (MRI). To image the subject internally the device performing the imaging is placed within the subject and the image is recorded from this device. One of skill in the art would understand that the principles disclosed herein could also be used for external imaging. In the embodiments below the magnetic resonance is generally imposed by an external MRI scanner such as those manufactured by Siemens or GE and understood to one of skill in the art. However, the magnetic resonance may be generated in any fashion, including by the apparatuses themselves. Further, the below embodiments are primarily directed to the imaging of the human body in a living subject. However, one of skill in the art would understand that the principles could be extended to any subject including, but not limited to, human beings or parts of human beings, non-human animals or parts of non-human animals, biological matter, or any other type of matter which would be desirable to image, such as, for example, imaging the interior of the walls of a building.

With reference to FIG. 1, an MRI imaging apparatus (100) according to one embodiment includes a substantially tubular member (99) having a distal end (105) and a proximate end (103) with a lumen (101) therebetween. The substantially tubular member (99) generally has an exterior surface (102) and an interior surface (116). There is also included an imaging coil (104) which may be of any design capable of receiving and/or transmitting magnetic resonance signals. The coil pictured in FIG. 1 is a loopless design. Loopless designed coils are known in the art, and a loopless coil could include, but is not limited to, designs such as those described by Ocali et al in U.S. Pat. No. 5,928,145 and by Lardo et al in U.S. patent application Ser. No. 09/536,090 "Magnetic resonance imaging guidewire probe," filed Mar. 24, 2000 (hereafter "Lardo '090"), the entire disclosures of which are herein incorporated by reference.

The apparatus shown in FIG. 1 shows the coil (104) embedded within the tubular member (99), but such a construction is by no means necessary. In other embodiments the coil could be on the interior surface (116) or the exterior surface (102) of the tubular member (99).

In one embodiment, an attachment point (108) to affix the sleeve to another device, such as a medical device (such as but not limited to a PTCA catheter, endoscope, balloon device for dilatation angioplasty, stent placement tool, drug delivery tool, intraluminal resecting tool, guidewires, electrophysiologic mapping instrument, atherotome for atherosclerotic plaque removal and debulking, another imaging device such as an MRI coil, and any other device designed for use within a catheter or sleeve) may be included at the distal end (105), and a connector hub (110) possibly with strain relief may be included at the proximal end (103). Attachment point (108) may be of any type for temporary or permanent attachment, and may comprise any type of connector for interfacing with the attached device known to one of skill in the art. An electrical transmission member, in this case a coaxial cable (114), connects the coil (104) to an MRI scanner (Not shown) for the transmission of signals between the scanner and the coil. In the embodiment in FIG. 1 the electrical transmission member is also embedded within the tubular member (99). In an embodiment, the coaxial cable (114) is connected to a decoupling circuit connector (112) and connects the coil (104) to a decoupling circuit (not shown). An example of a decoupling circuit to which the decoupling circuit connector could be attached is described in Lardo '090. In one embodiment, the connector hub (110) and decoupling circuit connector (112) are located at the proximate end, while the imaging coil (104) is located at the distal end. However, other arrangements of these elements relative to the ends (103, 105) will be readily apparent to one skilled in the art.

Figure 14:
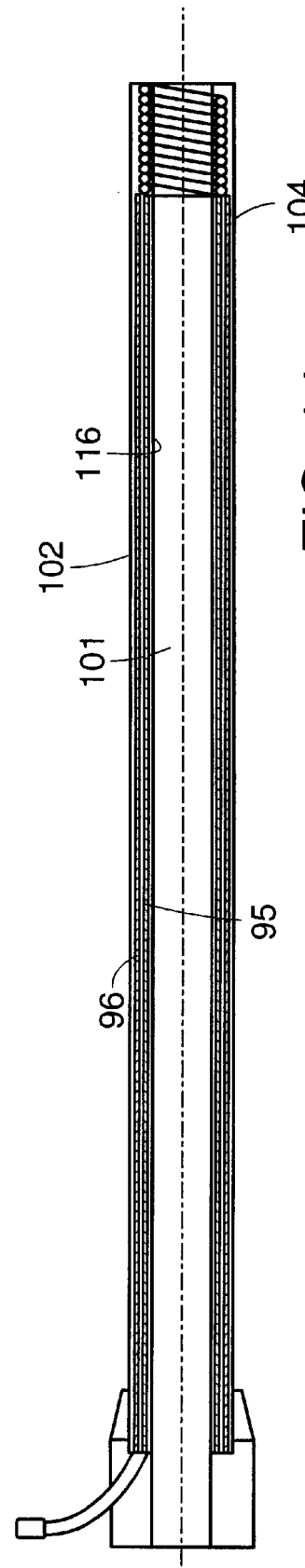
FIG. 14 shows a cross-section view illustrating an imaging sleeve.

An embodiment of the apparatus of the following construction is shown in FIG. 14. The coaxial cable (114) may be built in the walls of the tubing in form of a inner (95) and an outer (96) braid where the inner braid (95) acts as a core of the coaxial cable and the outer braid (96) acts as a primary shielding. This design may leave the lumen (101) entirely patent for delivering various devices e.g. guidewires, therapeutic catheters, contrast agents, and the like.

The antenna can be a loop, quadrature loop, loopless with the whip coiled or, as shown in FIG. 14A, loopless where the coil (104) comprises an extension of the inner braid (95) extending to the distal end (105) of the sleeve. In an embodiment, depicted by way of example in FIG. 14B, another layer of braiding can be provided over the primary shielding to act as a bazooka balun (97). Also another braiding connected to the ground (not shown) can be added below the core-braiding to prevent coupling/change loading conditions when devices are inserted and moved inside the sleeve.

In an embodiment, the braidings comprise copper, tanatalum or any other nonmagnetic material which will give a low susceptibility artifact under MR. In another embodiment, the braidings comprise gold, silver or any other metal plating on a polymeric surface or applied using different techniques such as, but not limited to, sputtering. In an embodiment, the metallic conductive layers may be electrically continuous, but need not be physically continuous.

The impedance of the coaxial cable created this way may generally be anywhere from 10–50 ohms. Also the distal end of the imaging sleeve can be formed in various shapes, for instance, for forming different guide catheters.

In an embodiment, the imaging sleeve further comprises a contrast agent to enhance the active tracking ability of the coil. The contrast agent is incorporated into the tubular member or the coil, for example, by applying a coating containing the contrast agent, blending the contrast agent with the material of the sleeve during or before extrusion, or other means readily apparent to one of ordinary skill in the art. This contrast agent may be incorporated throughout the entire sleeve or confined in a portion thereto. In active tracking, the sleeve images the anatomy around the device, including a broad signal from the coil, and the coil outline is bigger than the actual device. The contrast agent may reduce the outline so that the size of the device as seen on the image will approximate its true size. Examples of contrast materials include, but are not limited to gadolinium and dysprosium oxide, and any other MRI contrast materials known to one of skill in the art.

Data acquisition during imaging may occur in different modes. In an embodiment, high-speed data acquisition and display techniques may be employed when the coil is being used to locate the position of the sleeve relative to an anatomical structure of interest. Use of a contrast agent may be especially beneficial in this situation because the contrast material will generate a very intense signal in the MRI image. Image sampling may then occur at a faster rate. In another embodiment, high-resolution imaging mode is employed to generate the highest-quality image possible, and the speed of acquisition may be slower than in high-speed mode. Our aim is to generate the best quality image.

Figure 16:
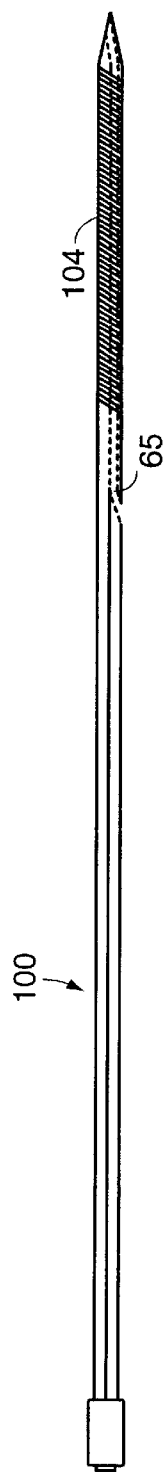
FIG. 16 shows a cross-section view illustrating an imaging monorail catheter.

In another embodiment, shown by way of example in FIG. 16, the apparatus comprises a rapid exchange or a monorail catheter, having an imaging sleeve (100) and a guidewire lumen (65) with 2 wire ports provided below the imaging coil (134). The imaging antenna can be a single loop, fixed or expandable, quadrature loop or a loopless design.

In an embodiment, the apparatus may further comprise additional substantially tubular members. For example, a second tubular member may be the guidewire lumen (65) as shown in FIG. 16. In another embodiment, a lumen is provided for deployment of additional medical devices, such as a balloon catheter or basket device. In an embodiment, the proximal end (103) has a plurality of ports providing access to, for example, the volume enclosed by the tubular member, a connection through which water or any other fluid may be discharged into the sleeve, a connector to the detector coil to change its shape, and other uses as will be apparent to one of skill in the art.

Figure 18:
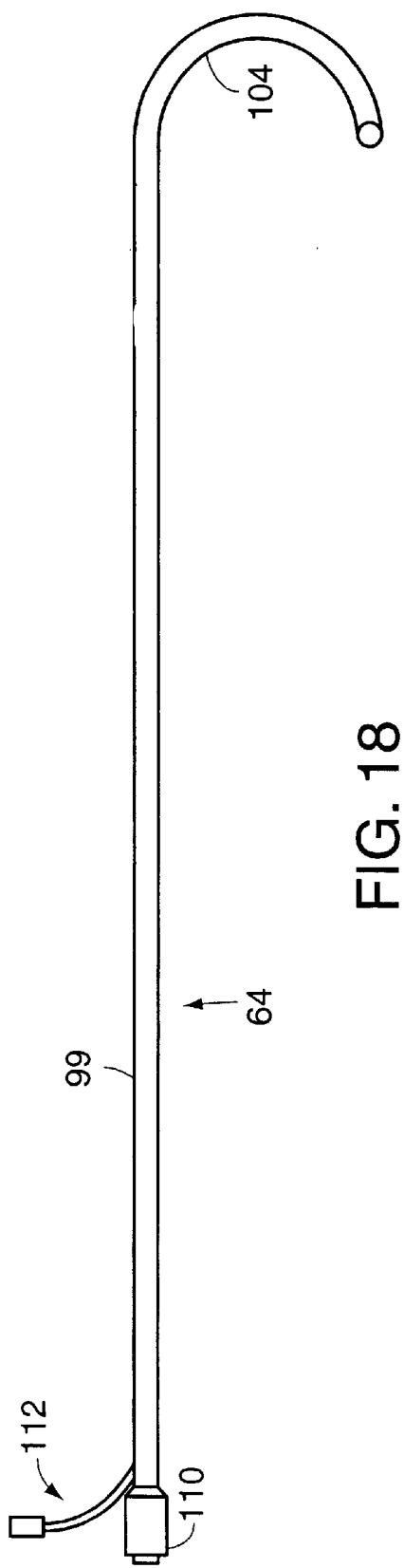
FIG. 18 shows a cross-section view illustrating an imaging guide catheter.

In an embodiment exemplified by FIG. 18, the sleeve may take the form of a guide catheter (64) similar to that used in typical angioplasty and angiography procedures. The guide catheter has a preformed shape to facilitate access into the right or left coronary artery systems. The sleeve may further comprise a lumen obstruction device, such as a balloon, to perform angioplasty. The sleeve may further comprise an embedded braid providing stiffness and torque control. The stiffness of the braid may vary from position to position in the sleeve.

In an embodiment, the tubular member is constructed of polymer. This could be a single polymer, or multiple polymers could be used. The reasons for selecting a particular polymer or combination of polymers would be apparent to one of skill in the art but could include controlling particular mechanical or electrical properties for any portion of the tubular member (99). Examples of suitable polymers are nylon, PEBAX, polyurethane, polyethylene, silicone polymers, fluoro-polymers, or other similar polymers known to those skilled in the art. Some or all of the length of the tubular member can be made up of single or multiple polymers so as to control mechanical properties over the length of the member. The apparatus can be coated on interior surface (116) and/or exterior surface (102) with appropriate coatings, e.g., hydrophilic coatings on the exterior surface and silicone on the inner surface to achieve further desired mechanical or electrical properties. Examples of suitable coatings include PVP, poly acrylic acid, and other hydrophilic-based polymers.

In an embodiment, the tubular member may be constructed so as to have varying stiffness at different positions. For instance, the distal end could be more flexible than the proximal end so as to help prevent injury to subject during insertion and placement of the sleeve.

In FIG. 1, the coil is created in a manner so as to allow for it to be able to image structure surrounding the distal end (105) of tubular member (99). One method of creating such a coil is described as follows. At a transition point (118), the coaxial cable (114) is terminated and its core (120) is extended onward and is coiled forming the coil (104). The coil (104) is depicted in FIG. 1 as a helical wound conductor by way of example. A secondary shielding (122) which in one embodiment is in the form of a braiding may be provided and is connected to the shielding of the coaxial cable at the distal end (105). The braiding may comprise a suitable electrical conductor at the MRI/MRS radio frequencies. Examples of suitable materials include copper, or a nickel titanium alloy commonly known as Nitinol plated with gold, silver (or alternate layers of gold, silver, or copper, and/or gold on nitinol), or copper, or may comprise an MR compatible stainless steel, or aluminum, or gold or silver coated MR compatible stainless steel.

The secondary shielding (122) can prevent the electrical and imaging properties of the coil from changing when the coil is attached to the tubular member. In addition, the braiding may provide electrical isolation from the devices used inside the sleeve. For example, an imaging guidewire inserted inside the sleeve may couple with the detector coil in the sleeve and cause imaging artifacts. In an embodiment, the secondary shielding (122) is electrically grounded and may thus prevent changes in loading conditions which might occur due to having another coil inside the imaging sleeve.

FIG. 1A depicts a proximal end (103) view of the assembly of FIG. 1, showing the relationship of the tubular member (99) with the coaxial cable (114) and the lumen (101) therein.

In an embodiment shown in FIG. 1B the coil is attached to the exterior surface (102) of the first tubular member (99) and a second tubular member (98) is placed co-axially with the first (S tubular member (99). This may be placed so as to provide an exterior covering of the coil (104) as is shown in FIG. 1B. This second tubular member (98) may be loose or may be bonded on the first tubular member (99). In an embodiment, the second tubular member (98) is loose and may move slideably along at least a portion of the length of the first tubular member (99).

Figure 2A:
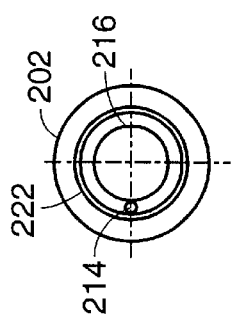
FIG. 2A shows a proximal end view of the embodiment depicted in FIG. 2.

FIG. 2 shows another embodiment employing a loop imaging coil (224) as coil (104). The exterior surface (202) and inner surface (216), connector hub (210), connector (212), and clip (208) may be as described in FIG. 1. The loop imaging coil (224) is similar to that described above, except that the loopless imaging component is replaced by the loop components, e.g., an imaging loop (226), tuning matching capacitors (228a, 228b), and a triaxial cable (214) to conduct the received signals to a scanner and incorporating a balun circuit. The secondary shielding (222) may be included in the loop antenna imaging sleeve. Tuning/matching capacitors can be distributed around the loop to improve performance, as for example depicted in the embodiment of FIG. 3 with a tuning/matching capacitor (340) at the distal end. A tuning/matching capacitor can also be added to the proximal end of the loop, or one tuning capacitor added at the distal end and one at the proximal end as depicted in FIG. 2 with tuning/matching capacitors (228a, 228b). FIG. 2A depicts a proximal end view of the instant embodiment, showing the relationship between the exterior (202) and interior (216) surfaces with the triaxial cable (214).

Figure 3:
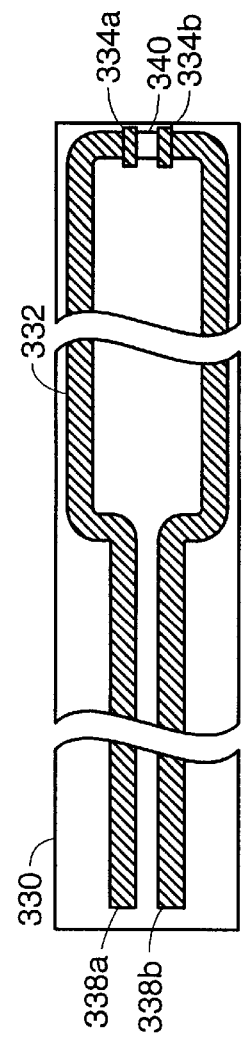
FIG. 3 shows a cross-sectional view illustrating one embodiment of a loop imaging coil.

The loop imaging coil (224) may be of any design known in the art, including those described by Atalar et al in U.S. Pat. No. 5,699,801 (hereafter "Atalar '801"), the entire disclosure of which is herein incorporated by reference, and by Atalar et al, U.S. Pat. No. 6,263,229 (hereafter "Atalar '229") the entire disclosure of which is herein incorporated by reference. FIG. 3 shows one embodiment of a loop imaging coil which may be used. In this embodiment, the detector coil resides on a flexible circuit board. The detector coil may reside on any substrate (330), made for instance of Kapton or other material known to one of skill in the art, and may be applied, for example by etching, depositing, or by some other process known to one of skill in the art. A copper conductor (332), distal pads (334a, 334b) for a tuning/matching capacitor and decoupling circuit (340), and proximal pads (338a, 338b) for connecting the coaxial cable (214) may also be present. In an embodiment, the copper conductor may have dimensions of at least 5 micrometers thick and 0.1 millimeters wide. In another embodiment, the copper conductor may have the dimensions of 18 micrometers thick and 0.7 millimeters wide.

FIG. 4 shows yet another embodiment employing another type of loop imaging coil, in this case a quadrature loop imaging coil (404). Two substantially orthogonal loops are used to improve the homogeneity of the coil reception in a substantially quadrature mode. One skilled in the art would understand that the coils may also be situated at angles other than substantially orthogonal. The tuning/matching capacitors (428a, 428b) may similarly be incorporated into the quadrature loop embodiments. The dimensions of the loop and the device will vary as according to the particular application, i.e. the procedure and anatomy of interest, and the image resolution desired. Quadrature loops are described in Atalar '229. FIG. 4A is a cut-section through line A—A of FIG. 4 and shows one arrangement of the two loop coils (407a, 407b) of the quadrature loop imaging coil (404).

FIG. 5 shows another embodiment which may be used in conjunction with a second medical device to be deployed within the lumen (501). The interior surface (516) of the present embodiment can be coated with a lubricious coating (542) as described above to facilitate fitting of the apparatus over another medical device, such as but not limited to a PTCA catheter, endoscope, balloon device for dilatation angioplasty, stent placement tool, drug delivery tool, intraluminal resecting tool, electrophysiologic mapping instrument, atherotome for atherosclerotic plaque removal and debulking, another imaging device such as an MRI coil, or any other device capable of deployment within a sleeve. The detector coil (504) may comprise a loopless imaging coil or a loop imaging coil of any type known in the art, including those types described above and by Ocali et al in U.S. Pat. No. 5,928,145, by Atalar '801, and by Atalar '229.

Such arrangement may be used whenever imaging of an anatomical region or structure is desired while advancing a device to the region or structure or while using the device to examine, characterize, sample, diagnose, treat, ablate, resect, or otherwise manipulate the structure or region in ways readily apparent to one of skill in the art. Use of MRI instead of visible light visualization may be particularly advantageous. A visible light camera requires an unblocked optical light path for visualization. Any devices in the lumen of a sleeve may themselves block this path and prevent visualization of the anatomical structure or region being manipulated. An MRI antenna, such as those disclosed herein, has no such requirement and thus may provide a complete and unimpaired image regardless of what device, if any, is present in the lumen of the sleeve. MRI may also provide imaging data of anatomical structure beneath the surface of the structure or region of interest. This additional data may be of considerable value to an operator of a device according to this embodiment. It may show, for example, evidence of tissue damage that would not be apparent by visible light visualization.

Figure 6C:
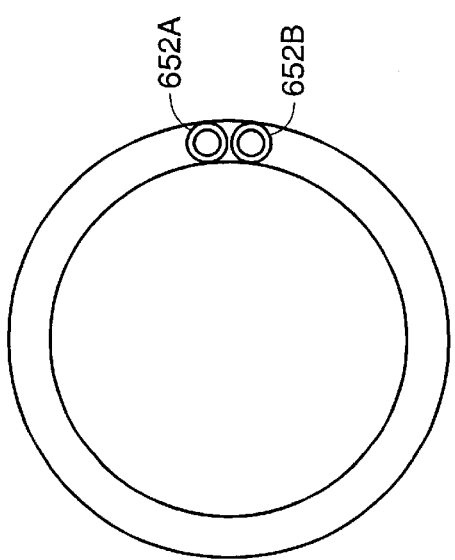
FIG. 6C shows a cross-sectional view of the embodiment depicted in FIG. 6 taken through the line C—C indicated in FIG. 6.

FIG. 6 shows yet another embodiment designed to provide an expandable loop imaging coil (644). A second tubular member (698) is slideably displaceable along the longitudinal axis of the sleeve between an extended position and a retracted position. When the second tubular member (698) is in its retracted state, the expandable loop imaging coil (604) is in its expanded state. When the second tubular member (698) is in its extended state, the expandable loop imaging coil (604) is in its collapsed state. The second tubular member (698) is depicted in the retracted position in FIG. 6 and in the extended state in FIG. 6A. Although in FIGS. 6,6A the loop is shown as being dimensionally different in the two states, that is not a necessary part of the design. The exterior (602) and interior (616) surfaces of the first tubular member (699) remain fixed relative to each other, and the interior surface (616) defines the lumen of the sleeve into and through which other devices may be inserted. As shown in FIG. 6B, the expandable imaging loop (644) can comprise a core (650) surrounded and encased by an insulator (648). In one embodiment, the insulator (648) comprises polymeric tubing. The core (650) is a pre-shaped superelastic electrically conducting material or metal such as a nickel titanium alloy commonly known as Nitinol. However, other known superelastic conducting materials including beryllium-copper alloy, and non-magnetic stainless steel are examples of materials that may be used. The pre-shaped superelastic material that forms the expandable loop is plated with gold, silver (or alternate layers of gold, silver and gold on nitinol) or other conductive metal to increase RF conductivity of the loop. It will be recognized that tuning capacitors may be incorporated in the distal or proximal or both ends of the loop as discussed for the embodiments of FIG. 2. FIG. 6C is a cut-section through line C—C of FIG. 6 and shows two ports (652a, 652b) which house the ends of the expandable imaging loop (644). Referring again to FIG. 6, even in its fully retracted state, the second tubular member (698) may house the ends of the expandable imaging loop (644), tuning/matching capacitor (628), ports (652a, 652b), and coaxial cable (614). This embodiment may further comprise a connector (612), which may be a BNC connector or mini-BNC connector for connection to an MRI machine, a decoupling circuit, or other apparatus (not shown). The expandable imaging loop (604) may comprise any loop imaging coil design known to the art, including all described above and all others described by Ocali et al in U.S. Pat. No. 5,928,145, in Atalar '801, and in Atalar '229. An expandable loop antenna can also be of a loopless design in an embodiment.

Figure 6D:
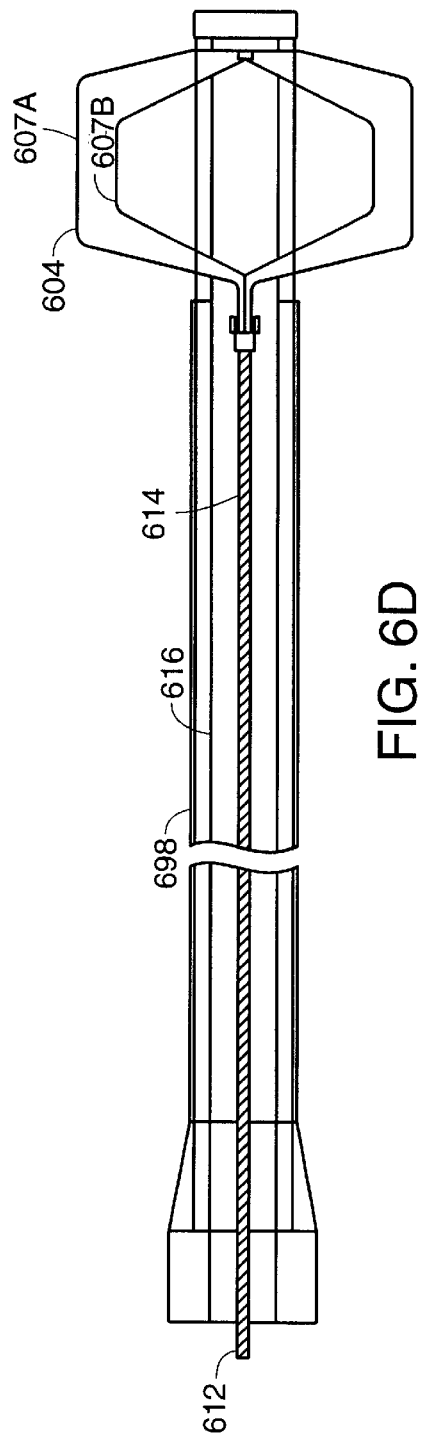
FIG. 6D shows a cross-sectional view illustrating an imaging sleeve according to an embodiment having an expandable quadrature loop imaging coil in its expanded state.
Figure 6E:
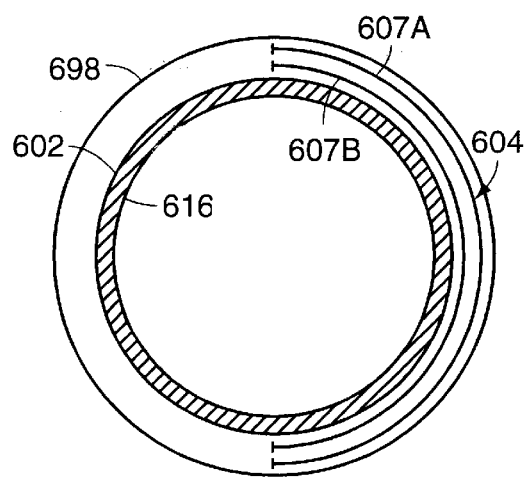
FIG. 6E shows a right-end cross-section view illustrating an imaging sleeve according to an embodiment having an expandable quadrature loop imaging coil in its collapsed state.

FIG. 6D shows an embodiment of the sleeve in which the expandable imaging loop (604) comprises a quadrature loop coil. The two loops (607a, 607b) of the expandable imaging loop (604) may be nested in their collapsed state in a substantially orthogonal manner similar to that illustrated in FIG. 4A for the two loop coils (407a, 407b). As shown in FIG. 6E, the loop coils (607a, 607b) may also be nested side-by-side in their collapsed state. When the second tubular member (698) is retracted, one of the two loop coils (607a, 607b), for example loop coil (607a) is mounted, spring-loaded, or otherwise attached in such a way that it rotates to or otherwise assumes a substantially orthogonal orientation relative to, for example, loop coil (607b) as the quadrature loop coil (604) transitions to its expanded state. Other arrangements of the two loop coils will be readily apparent to one skilled in the art.

Considering once again FIG. 6, to place the expandable imaging loop (604) in its collapsed state, the second tubular member (698) may be slid into its extended position over the expandable imaging loop (604) so that the loop is caused to contract. The collapsed state of the expandable imaging loop (604), as shown in FIG. 6A, may be used during insertion of the sleeve and advancement of the sleeve to a point or anatomy of interest. This may provide the advantage of having a low-profile device during advancing and retracting from the anatomy of interest, and an expanded imaging loop once the apparatus is situated in the anatomy of interest for improved imaging for improved diagnostic value. In one embodiment, the expandable imaging loop (604) comprises a superelastic material, such as Nitinol, having a very high degree of "memory." This allows for the loop to have a precise, predetermined separation when the loop is expanded again. Because this separation remains essentially constant throughout many cycles of loop expansion and contraction, the tuning and matching components can be set to constant, finely tuned settings.

The expanded state may be used during image acquisition, and provides improved SNR over other low-profile coils. To place the expandable imaging loop (604) in its expanded state, as shown in FIG. 6, the second tubular member (698) is slid to the retracted position at which it may cover only the proximal ends of the expandable imaging loop (604).

For the loop coils the area in the loop and therefore the distance of separation between the parallel conductors determines the image quality or SNR. In general, the greater the separation, the greater the SNR, which provides an SNR advantage for the expandable loop compared to a fixed loop (FIG. 2) if the location of interest is suitable for its deployment. The expandable loop can be made in various configurations e.g. to open to a specific dimensions, expand depending on the anatomical cavity available, or within the lumen of another device or vessel.

The expandable loop and any of the other coils known in the art or disclosed herein may be encased in a body lumen obstruction device, for example, a balloon, or some other similar device known to one of ordinary skill in the art. Such an obstruction device may be used to prevent flow of any material through the lumen in which the apparatus is situated. For example, an obstruction device may be deployed while the apparatus is in a blood vessel. In this case, the obstruction device would prevent flow of blood through the blood vessel. Specifically, the device may be used in any of the coronary arteries or principal divisions thereof to guide, with the detector coil, a angioplasty means such as a lumen obstruction device to a diseased artery. The balloon can be circular or elliptical with variable or fixed diameter as per inflation pressure. However, since tuning matching is specific for a particular separation, if the separation varies, the device may require retuning for optimum performance.

Figure 7:
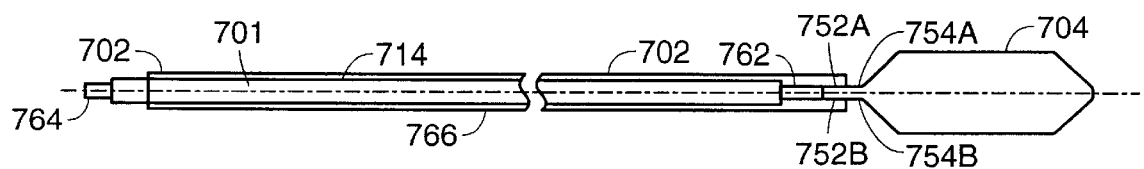
FIG. 7 shows a cross-sectional view illustrating an imaging probe according to an embodiment having an expandable loop imaging coil in its expanded state.

The expandable loop may also be employed in an MRI imaging probe designed, for example, to be deployed within the MRI sleeve as a guidewire, or as any of the probes described in Atalar '801. As shown in FIG. 7, such a probe can comprise an detector coil (704), the ends (754a, 754b) of which are connected by ports (752a, 752b), to a tuning/matching circuit (762) coupled to a coaxial cable (714) that conducts signals received by the expandable imaging loop (704) to an MRI scanner or the like, via a BNC connector or other connector (764). An interface system, being for example a flexible circuit board, may be used to mount the tuning/matching circuit (762) and a decoupling circuit. Flexible polymeric tubing (766) houses the ends (754a, 754b) of the expandable imaging loop (704), ports (752a, 752b), tuning/matching circuit (762), and coaxial cable (714).

Figure 7A:
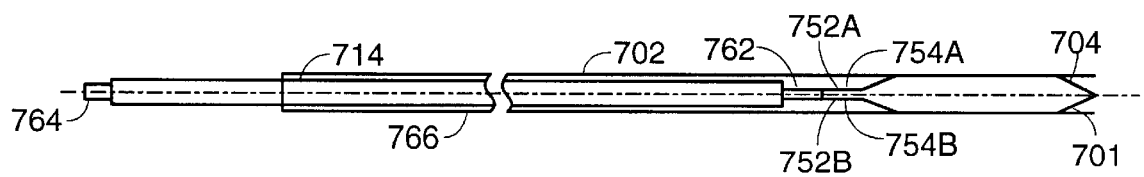
FIG. 7A shows a cross-sectional view illustrating an imaging probe according to an embodiment having an expandable loop imaging coil in its collapsed state.

A tubular member (702) having a lumen (701) encases the assembly and in one embodiment comprises a polymeric tubing for access to areas some distance from the point of entry. However, the material may be metallic for use as a trocar or introducer to guide placement of interventional tools through it. To place the detector coil (704) in its expanded state, as shown in FIG. 7, the tubular member (702) is slid to a position at which it may cover only the proximal ends (754a, 754b) of the detector coil (704). Therefore, the at least part of the detector coil (704) is positioned outside the lumen (701) of the tubular member (702) when in its expanded state. The expanded state may be used during image acquisition, and provides improved signal-to-noise ratio over other low-profile probes. FIG. 7A shows a device according to the embodiment of FIG. 7 but wherein the expandable imaging loop (704) is in its collapsed state and is wholly or partially contained within the lumen (701).

To place the expandable imaging loop (704) in its collapsed state, the tubular member (702) is slid over the expandable imaging loop (704) so that the loop is caused to contract. The collapsed state may be used during insertion of the device and advancement of the device to a point or anatomy of interest. In one embodiment, the expandable imaging loop (704) comprises a superelastic material, such as Nitinol, having a very high degree of "memory." This allows for the loop to have a precise, predetermined separation when the loop is expanded again. Because this separation remains essentially constant throughout many cycles of loop expansion and contraction, the tuning and matching components can be set to constant, finely tuned settings.

Figure 8:
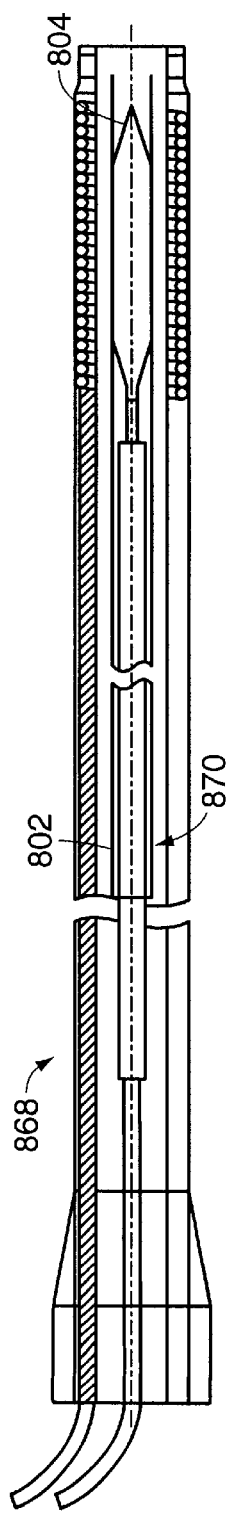
FIG. 8 shows a cross-sectional view illustrating a combination imaging device according to an embodiment having a loopless imaging coil embedded in the sleeve and a probe insert having an expandable loop imaging coil in its collapsed state.
Figure 8A:
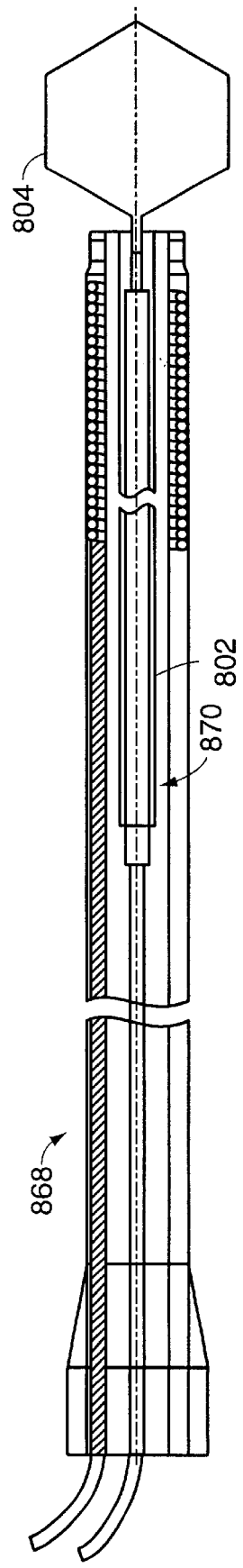
FIG. 8A shows a cross-sectional view illustrating a combination imaging device according to an embodiment having a loopless imaging coil embedded in the sleeve and a probe insert having an expandable loop imaging coil in its expanded state.

The imaging probe featuring the expandable imaging loop may be used in conjuction with any of the MRI sleeves herein using any of the imaging coil designs described herein and in the above given references. The expandable imaging probe, in its collapsed state, may be inserted into an MRI sleeve as shown in FIG. 8 with a loopless sleeve coil. One skilled in the art would understand that any type of imaging coil known in the art may be employed in the MRI sleeve component of the combination device. The combination device comprises an MRI sleeve (868) and an expandable probe (870). The combination device may be advanced to the anatomy of interest, perhaps through narrow-lumened structures such as blood vessels, esophagus, small intestine, biliary tree members, and others that are obvious to practitioners of the art. Once the combination device is in position, the expandable probe (870) may be advanced so that the coil region (804) protrudes from the sleeve. As depicted in FIG. 8A, the coil region (804) may be brought into its expanded state by retracting the tubular member (802) to expose the coil region (804). In another embodiment, the sliding sheath (802) may be omitted, with the interior surface (816) of the sleeve holding the expandable probe (870) in its collapsed state. The expandable probe (870) may also be placed in its expanded state by advancing the expandable probe (870) so that the coil (804) protrudes from the sleeve (868).

The use of an expandable probe with an MRI sleeve provides advantages over the use of either alone. For example, the imaging sleeve may be used to provide visualization of surrounding tissue and of itself as it is introduced into a body and advanced to the structure of interest. Once the combination probe is in place, the expandable probe insert may be advanced and expanded, providing increased SNR over lower-profile coils during image acquisition. Alternatively, the expandable probe may be advanced through a structure of such limited dimensions that the sleeve itself is excluded. In this case, the inner surface of the sleeve is used to maintain the collapsed state.

Figure 9:
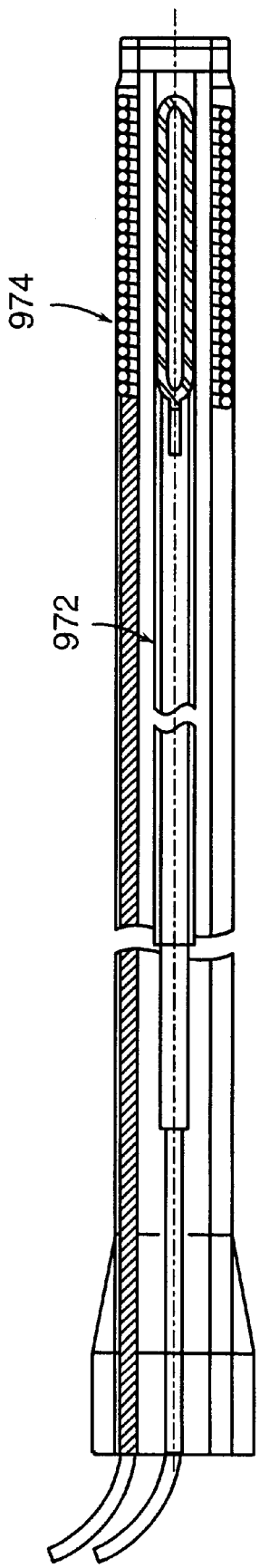
FIG. 9 shows a cross-sectional view illustrating a combination imaging device according to an embodiment having a loopless imaging coil embedded in the sleeve and a probe insert having a loop imaging coil.
Figure 9A:
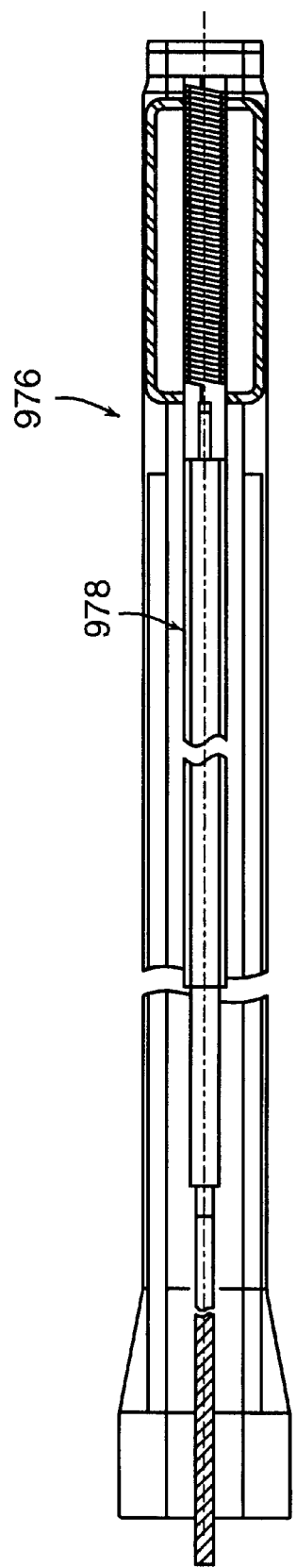
FIG. 9A shows a cross-sectional view illustrating a combination imaging device according to an embodiment having a loop imaging coil embedded in the sleeve and a probe insert having a loopless imaging coil.

Probe inserts used in combination with an MRI sleeve may also comprise nonexpandable MRI probes dimensionally adapted to be inserted into a sleeve or catheter. The probe insert coil and the MRI sleeve coil may both be of any type known in the art, including those described in the above-named references. FIG. 9 shows an embodiment in which a loop imaging coil probe (972) is inserted in a loopless imaging coil sleeve (974). FIG. 9A shows another embodiment in which a loopless imaging coil probe (978) is inserted in a loop imaging coil sleeve (976). The MRI sleeve and MRI probe may both comprise one or more imaging coils of any types known in the art or disclosed herein. Other combinations will be readily apparent to one skilled in the art.

Figure 10A:
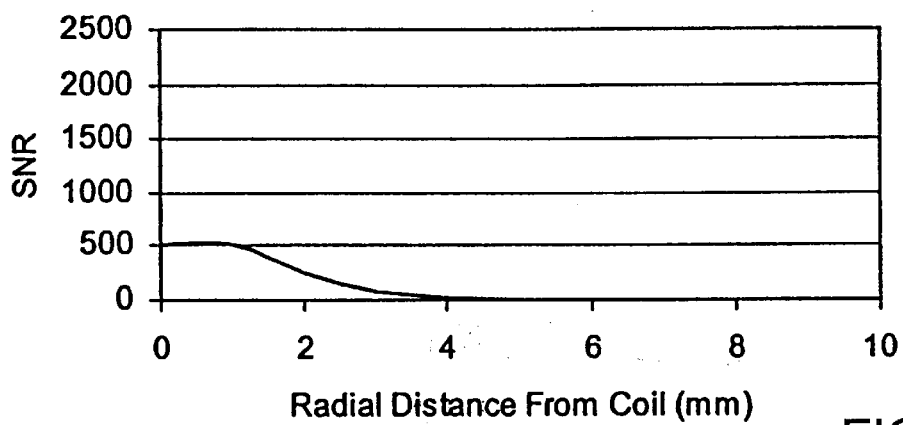
FIGS. 10A, 10B, 10C are schematic representations of signal strength as a function of position along loop, loopless, and combination imaging loops, respectively.
Figure 10B:
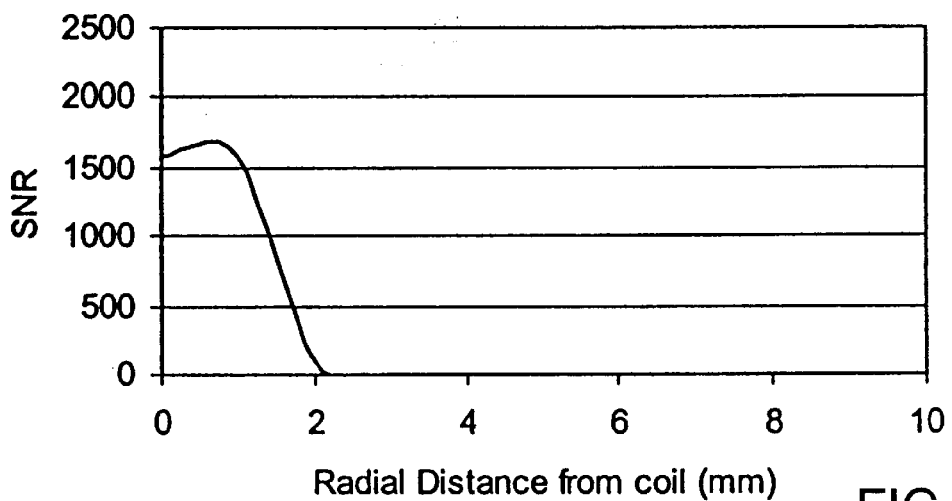

Combinations of MRI coils such as those described above, and such as certain embodiments of which are depicted in FIGS. 8, 8A, 9, 9A may offer superior SNR and imaging sensitivty along the length of the imaging coil combination compared to a single coil alone. Loop imaging coils offer near field high resolution imaging, while loopless coils provide broad field imaging at lower resolution. FIG. 10A depicts schematically the sensitivity profile of a loopless imaging coil. Signal stength reaches a peak in a fixed diameter region along the length of the imaging coil. This provides excellent visualization in only a confined area. In contrast, FIG. 10B shows a schematic sensitivity profile of a loop imaging coil. While not approaching the peak signal strength achieved by the loop design anywhere along its length, the loopless coil design provides limited sensitivity distributed along its length. By combining two imaging coils, one of each design, (i.e., a loop sleeve with a loopless probe, or a loopless sleeve with a loop probe) a sensitivity profile combining the strength properties of each design is achieved, as depicted schematically in FIG. 1C. Combinations of a loopless probe and a loopless sleeve and of a loop probe and loop sleeve accentuate the signal sensitivity properties of the respective designs. In all combinations, any loop or loopless coils may be of any types and designs known in the art or disclosed herein, including but not limited to, loopless coil, helical coil, solenoid loop, loop, quadrature loop, expandable loop, or expandable quadrature loop.

As described above, in an embodiment, all coils may be located inside a subject to be imaged. In another embodiment, at least one coil of a combination may be situated outside the subject to be imaged, and at least one other coil may be inside the subject. In yet another embodiment, all coils may be located outside the subject to be imaged.

The signals from the imaging coils may be combined through the use of a controller, such as, but not limited to, a computer, computer software, image acquisition systems on the MRI scanner, or any other systems known to one of skill in the art.

Figure 15:
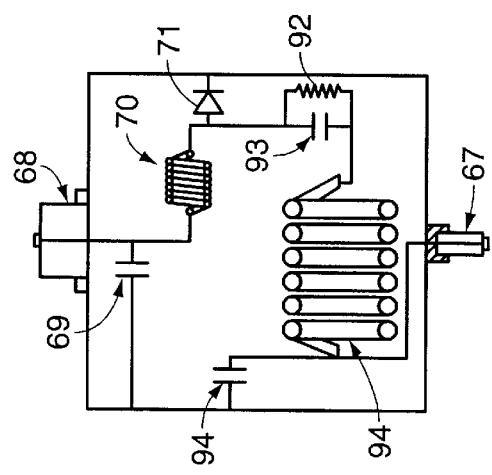
FIG. 15 shows an embodiment of an interface circuit.

FIG. 15 depicts one embodiment of an inter ace circuit. The interface circuit, when used in conjunction with a loop detector coil enables the loop coil to perform as a combined loop loopless antenna. The interface circuit may comprises, for example, a BNC connector (68), a micro BNC receptacle (67), balun cable trap (94), decoupling capacitor (93), DC regulating circuit (92), PIN diode (71), and a tuning/matching circuit having an inductor (70) and capacitor (69). The interface circuit may be connected to any loop coil. This changes the SNR characteristics of the coil so that it behaves similar to a loop+loopless coil (combined coil). The loop coils have matching tuning and decoupling circuits on the coil itself. The circuit described above makes it perform as a loopless antenna+a loop antenna. The cable trap (94) acts as a balun for both the loop and the loopless antennas. The decoupling circuit in the box as described above decouples the loopless antenna and allows the DC current to flow through to decouple the loop antenna. This DC flows through the resistor or an inductor in the circuit (92) activating the PIN diode (71) on the coil. The output of both the coils is then matched and tuned by the matching tunig circuit in the box (inductor 70, capacitor 69).

Figure 10C:
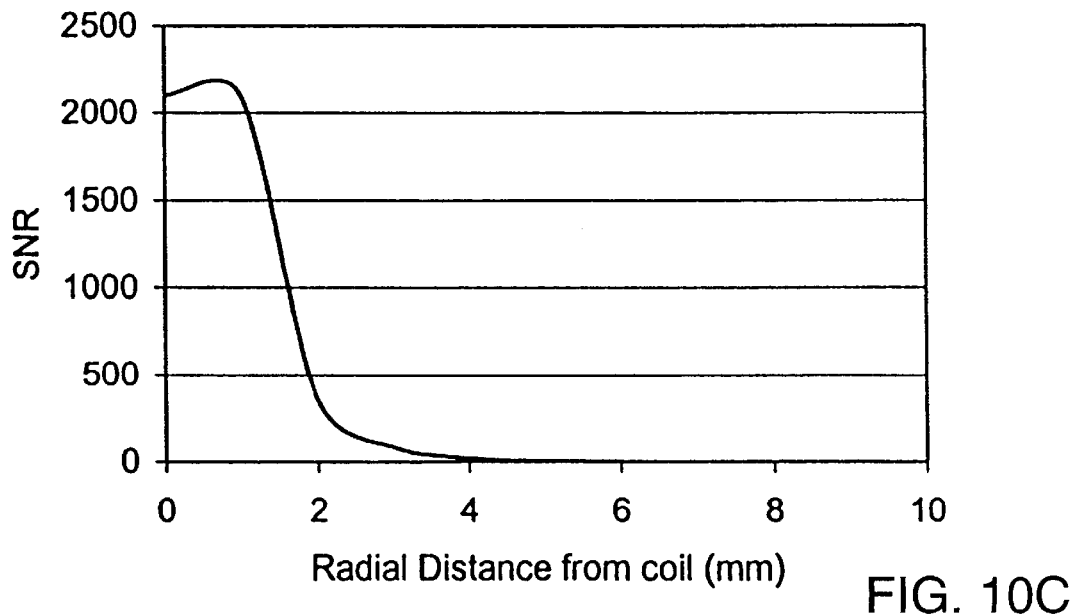

Combinations of loop and loopless imaging coils may be incorporated directly within the MRI sleeve itself. Such a combination provides the advantages of improved signal strength and imaging sensitivity as depicted schematically in FIG. 10C, but also provides for the simultaneous use of another medical instrument deployed in the lumen of the MRI sleeve. FIG. 11 depicts one exemplary embodiment. A loop imaging coil (1180) connected to a loop coil coaxial cable (1184) and a loopless imaging coil (1182) connected to a loopless coil coaxial cable (1114) may both be embedded in a tubular member (99), similarly as described for the embodiments of FIGS 1,2. The lumen (101) may remain patent for the passage of medical devices as described above. FIG. 11A depicts a left-end view of the embodiment of FIG. 11, showing this relationship. In all combinations, any loop or loopless coils may be of any types and designs known in the art or disclosed herein, including but not limited to, loopless helical coil, solenoid coil loop, loop, quadrature loop, expandable loop, or expandable quadrature loop.

In another embodiment, an MRI sleeve comprises at least one loop imaging coil and at least one loopless imaging coil embedded in the tubular member (99). The imaging coils may each be of any type known in the art or disclosed herein, including but not limited to the loop coil, quadrature loop coil, expandable imaging loop coil, and loopless imaging coil.

In yet another embodiment, a combination device comprises an MRI sleeve having at least one loop imaging coil and at least one loopless imaging coil embedded in the tubular member (99) and an MRI probe of any design known in the art or disclosed herein. This results in a combination having at least three coils. Combinations having greater than three coils may also be fashioned and are readily apparent to one of skill in the art.

Figure 13:
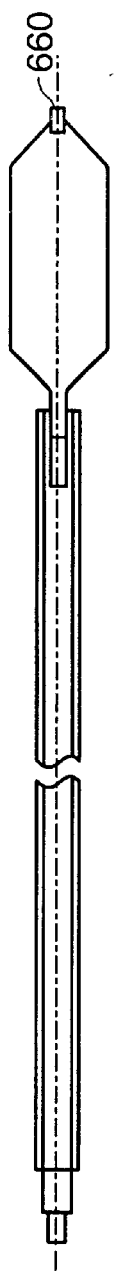
FIG. 13 shows a cross-sectional view illustrating an arrangement of the series capacitor of a tuning/matching circuit of the invention according to an embodiment having a loop imaging coil.

In general, it is useful, for the purposes of optimizing SNR and minimizing electromagnetic interactions between the imaging sleeve antennae and other coils and antennae to interface the imaging sleeve to the MRI scanner via one or more decoupling tuning/matching circuits and/or a balun. The tuning and matching capacitors can be placed in a variety of locations that are apparent to those skilled in the art and can be determined without undue experimentation. One embodiment is shown in FIG. 12, in which the ends (654a, 654b) of any type of loop imaging coil are attached to the coaxial cable (614) by a tuning/matching circuit comprising a capacitor in parallel (658) and a capacitor in series (660). The capacitor in series (660) may also be placed anywhere along the loop, for example, at the distal end of the loop. FIG. 13 depicts an embodiment in which the capacitor in series (660) is placed at the distal end of the coil. Such a positioning can improve imaging performance of the sleeve.

Each such configuration provides unique SNR properties, which will be apparent to those of ordinary skill in the art. The decoupling circuit (diode) in one embodiment is placed at the proximal end of the probe or in a suitable position with respect to the antenna to achieve maximum decoupling.

The MRI sleeve in an embodiment offers physicians and surgeons the opportunity to gather MR images for examination of anatomy, diagnosis, image-guided biopsy, and for guiding therapies such as minimally-invasive intervention, and surgery. Other applications will be readily apparent to one skilled in the art. The sleeve can be used with any MRI compatible surgical device of the physician or surgeon's choice, including additional MRI devices. Any inserted devices can be easily withdrawn and replaced by other devices as needed, for example, if a biopsy is followed by a surgical procedure during a single intervention. The metallic properties of the antenna in the sleeve renders it visible under x-ray which can also be used to determine its location in the body, if desired. For example, if the MRI apparatus to which a device according to the present invention is connected were to fail during use, MRI sleeves according to the invention could still be localized using X-ray imaging. The MRI sleeve may also be used as a locatable catheter in circumstances in which the use of MRI is inappropriate. For example, in subjects who have contraindications for MRI use (such as pacemakers or implanted prostheses containing ferromagnetic elements) the MRI sleeve may still be of utility because its location may be determined using X-ray imaging without actually exposing the subject to the magnetic fields required in MRI acquisition.

An MRI sleeve according to an embodiment may also be used in conjunction with any of the imaging guidewires disclosed in Lardo '090.

In one typical application, the sleeve is mounted on a commercially available MRI compatible surgical device, for example, an endoscope or laparoscope, which is then inserted into the body and advanced, for example, into the gastrointestinal (GI) tract for examination, image-guided biopsy, or minimally-invasive surgery. The imaging sleeve can be used with a trocar or other surgical device for minimally-invasive surgical procedures. The sleeve may also be used in combination to introduce another instrument or be used within the lumen of an endoscope or laparoscope to allow viewing through the wall, not attached to the end of an instrument.

The imaging sleeve offers the advantage of being useful with many medical devices e.g. MRI compatible endoscopes, laparoscopes, minimally invasive surgical tool (for example, trocar), and a single sleeve can be usable with multiple devices. It can be used independently as an access device for introducing surgical devices to the site of interest. MRI and endoscopy can be done simultaneously, thus providing a direct correlation and correspondence between visual surface information and the underlying anatomy and function detectable by MRI. Devices according to the invention can also be coupled with computer-integrated and guided surgical techniques. The invention has the capability to provide the minimally-invasive surgeon with a real-time three-dimensional view of the area of surgery. Other particular applications of the present invention include, esophageal imaging of the coronary arteries, imaging the prostate, urinary tract, bladder, GI tract, vasculature etc. The field of view possible by use of the sleeve or combinations of antennas of the invention is generally much larger than that provided by surface coils or other imaging modalities.

The present invention provides significant advantages over other devices. The low profile of the antennae according to the invention allow placement in small or narrow anatomies of interest, e.g., vasculature and GI tract. A high SNR can be obtained, using the invention, which provides for improved resolution and image quality. For vascular applications where an uninterrupted supply of blood is important to prevent hypoxic damage to tissues supplied by the vascular member in question, the device of the invention can be used without blocking the flow of blood, thereby allowing it to be held in vascular locations for relatively long periods of time without causing or risking tissue damage or necrosis. In addition, devices according to the invention may be used in combination with or function as the principal coronary or peripheral interventional tools, such as introducers, guide catheters, PTCA balloons, plaque removing devices such as atherectormy, drug delivery catheters, gene delivery catheters, radiation catheters, stent placement, and other applications readily apparent to one of ordinary skill in the art. The balun, matching, tuning and decoupling circuit can be placed close to the loop, thereby reducing signal loss.

Figure 17:
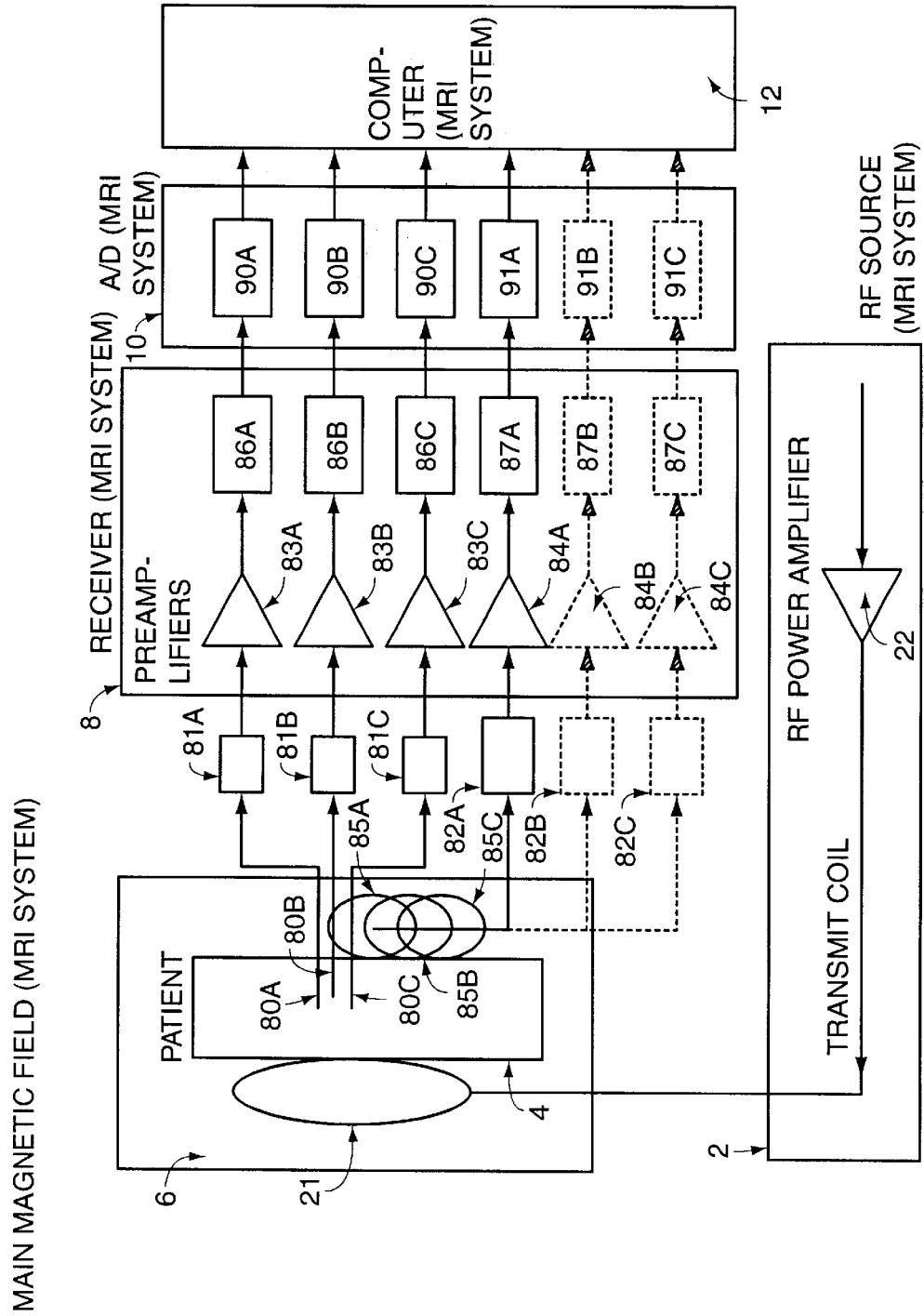
FIG. 17 shows an embodiment of a multichannel MM system.

Referring now to FIG. 17 which depicts an embodiment of a multi-channel MRI system suitable for exciting the exciting and receiving MRI systems detected by the aforementioned inventive devices. The figure depicts in greater detail the "RF source", "patient", "magnetic field", "receiver", "A/D converter", and "computer" sections numbered 2, 4, 6, 8, 10 and 12 of FIG. 1 of Atalar '801. The magnetic field 6, is produced by magnet means with field strength in the range 0.1 to 4 Tesla, but more typically from 0.3 Tesla to 3 Tesla as used for whole body clinical MRI. We now describe the multi-channel MRI system for using the aforementioned MRI probes in conjunction with conventional external coils, and how it is preferably used.

In an embodiment, patient or object to be studied 4 is placed in the magnetic field generated by the MRI system 6. MRI signals are excited by RF source 2, which includes RF power amplifier means 22 and transmit coil means 21 known to those skilled in the art. External 10 MR detector coil means 85a, and/or 85b and/or 85c and the like are initially used to detect said excited signals. The external MR detector coil can be a single surface coil 85a, or multiple coils for detecting signals either serially or in a parallel imaging configuration such as that known as a phased-array as described by P. B. Roemer et al in the journal "Magnetic Resonance in Medicine", Volume 16, pages 192–225, 1990. The MRI signals from the coils pass through tuning and transmit/receive switches 82a, 82b, 82c and the like and are fed to the receiver 8, which includes preamplifier means 84a, 84b, 84c and the like and analog or digital receiver means 87a, 87b, 87c etc. The low noise preamplifiers 86a, 86b, 86c etc and 87a, 87b, 87c etc of the MRI system each have gain and noise-figures substantially equivalent or comparable to individual preamplifiers conventionally used in MRI and known to those skilled in the art. The signals are digitized in 10 and fed to computer 12 where the image signals are reconstructed and displayed using Fourier reconstruction or other techniques known to those in the art, and displayed on display means 16 of FIG. 1 of Atalar '801, which can be a cathode ray tube. In the context of an MRI exam employing the inventive devices for internal MRI described above and in FIGS. 1–13 of the present application, the displayed images are used for visualizing the internal anatomy for the purpose of placement and introduction of the internal MRI coils.

At or before the time that it is desirable to visualize images generated from the internal MRI coils, the one or more outputs of the aforementioned internal MRI coils are input to tuning and matching means and transmit/receive switching means 81a, 81b, 81c etc, examples of component designs which are described in FIGS. 4, and 5 of Atalar '801, and FIGS. 3 and 7 of Ocali et al, U.S. Pat. No. 5,928,145, and included herein by reference in its entirety. The outputs of each device is then each fed to a separate channel of the multi-channel receiver which includes preamplifier means 83a, 83b, 83c etc, receiver means 86a, 86b etc, and is digitized by 90a, 90b etc before being fed to computer means 12. While it is envisaged that the gains of preamplifiers 83a, 83b, 83c etc, used for amplifying the internal coils will generally be comparable to that of 84a, 84b etc for the external coils, in some circumstances, the inherent voltage signal strength between internal and external coils and between different internal coils may differ and it may be desirable to adjust the gain of amplifiers 83a, 83b, 83c etc by automatic or fixed means, for example, under computer control, or by inserting an additional amplifying means in the appropriate receiver channel, in order to improve image quality. The signals presented in the computer are then reconstructed in one of 3 ways. Either the signals from one of the input channels is selected and reconstructed individually, or the signal from one of the coils and a desired signal from one of the other coils are alternately reconstructed and displayed, or the signals from 2 or more of the coils, including a possible choice of both an internal and an external coil are reconstructed in parallel by treating them, for the purpose of image reconstruction, as phased-array signals.

Imaging by this means may proceed in a rapid fashion while the internal coils are being introduced into the object being studied, for example, employing a phased-array reconstruction of all coils that provide sensitivity to a region of interest in the body. Once at a region of interest, it may be desirable to switch to an internal coil with a smaller field of view to acquire high resolution information and/or to perform an interventional procedure at the local site. After visualizing the desired structures, it may then be desired to reposition the internal coil under image guidance, at which point one may switch back to using multiple coils in parallel with a larger field of view, before switching again to one or more of the internal coils to provide high-resolution imaging. Accordingly it is a desirable feature of the MRI computer means 12, to include means of switching and selecting between one and more of the various input devices 80a, b, c . . . and 85a, b, c . . . etc via software under operator control.

Another embodiment provides an apparatus for internally imaging using MRI, comprising a detector coil for internally imaging using MRI, and a trigger mechanism in communication with the detector coil, wherein activation of the trigger mechanism causes the detector coil to change from a collapsed state to an expanded state. In an embodiment, the trigger mechanism comprises a pull wire. In an embodiment, the detector coil in the collapsed state is dimensionally different from the detector coil in the expanded state.

Various alternative embodiments are envisioned and within the scope of the invention. The imaging sleeve of the invention can be used with different puncture needles used to access the cranial anatomy, with a minimally invasive device for vein harvesting, and sleeves fabricated to fit over endoscopes for GI imaging, trocars, devices used for robotic guided surgery, devices for minimally invasive cardiac surgery (valve replacement, bypass grafts, etc.), orthopedic surgical devices, urethral catheters, and linear extrusion catheters for colonoscopy and lower GI tract diagnosis.

Therefore, while the invention has been particularly shown and described with reference to a number of embodiments thereof, it will be understood by those skilled in the art that various changes in form and details may be made therein without departing from the spirit and scope of the invention.

We claim:

1. An apparatus for imaging using magnetic resonance imaging (MRI) comprising:
    a substantially tubular member having a distal end, a proximal end, and a lumen extending between said distal and said proximal end; and
    a detector coil for imaging, using magnetic resonance imaging (MRI);
    wherein said tubular member is moveable between at least two states relative to said detector coil, such that in said first state said detector coil is positioned within said lumen and in said second state said detector coil is extended beyond said lumen to permit imaging.

2. The apparatus of claim 1, wherein said detector coil includes at least one of a loop expandable coil, a quadrature loop expandable coil, or a loopless expandable coil.

3. The apparatus of claim 1, wherein said detector coil in said second state is expanded.

4. The apparatus of claim 1, wherein said detector coil in said first state is dimensionally different from said detector coil in said second state.

5. The apparatus of claim 1, wherein said detector coil is placed in a subject in said first state and detects magnetic resonance in said subject in said second state.

6. The apparatus of claim 1, wherein said detector coil is dimensionally adapted for insertion into and advancement through a catheter.

7. The apparatus of claim 1, wherein said detector coil can image in said first state.

8. The apparatus of claim 1 further comprising a body lumen obstruction device.

9. The apparatus of claim 1 further comprising an interface system having a tuning/matching circuit and a decoupling circuit, said interface system interposed between said detector coil and an MRI imaging system.

10. A system for imaging using magnetic resonance imaging (MRI) comprising:
    means for placing a first and a second detector coil internal to a subject and adjacent to an area for imaging; and
    means for moving said first detector coil relative to said second detector coil so that the coils in combination detect magnetic resonance.

11. An apparatus for internally imaging using magnetic resonance imaging (MRI) comprising:
    a first substantially tubular member having a distal and a proximal end and an interior and exterior surface; and
    a detector coil attached to said tubular member for internally imaging, using magnetic resonance imaging (MRI).

12. The apparatus of claim 11 wherein said detector coil is attached in proximity to said distal end of said first tubular member.

13. The apparatus of claim 11 wherein said detector coil is on said exterior surface of said first tubular member.

14. The apparatus of claim 11 wherein said detector coil is embedded within said first tubular member.

15. The apparatus of claim 14 further comprising an electrical transmission member for electrically connecting said detector coil to an MRI scanner.

16. The apparatus of claim 15 wherein said electrical transmission member is on said exterior surface of said first tubular member.

17. The apparatus of claim 15 wherein said electrical transmission member is a coaxial cable.

18. The apparatus of claim 17 wherein said coaxial cable is embedded within said first tubular member and comprises a first braid and a second braid.

19. The apparatus of claim 18 further comprising a third braid.

20. The apparatus of claim 15 wherein said electrical transmission member is a triaxial cable.

21. The apparatus of claim 11 further comprising a second substantially tubular member placed co-axially with said first substantially tubular member.

22. The apparatus of claim 21 wherein said second substantially tubular member is slideably related to said first substantially tubular member.

23. The apparatus of claim 11, wherein said detector coil includes at least one of a loop coil, a quadrature loop coil, a loopless coil, a loop expandable coil, a quadrature loop expandable coil, or a loopless expandable coil.

24. The apparatus of claim 11, wherein said first substantially tubular member is dimensionally adapted for insertion into a body.

25. The apparatus of claim 11, wherein said first substantially tubular member is dimensionally adapted for passage of medical devices therein.

26. The apparatus of claim 11, wherein said detector coil resides on a flexible circuit board.

27. The apparatus of claim 11, wherein said detector coil comprises a solenoid.

28. The apparatus of claim 11, further comprising a probe adapted for passage within a lumen within said interior surface.

29. The apparatus of claim 28, said probe including a probe detector coil.

30. The apparatus of claim 29 wherein said probe detector coil includes at least one of a loop coil, a quadrature loop coil, a loopless coil, a loop expandable coil, a quadrature loop expandable coil, or a loopless expandable coil.

31. The apparatus of claim 11, further comprising an attachment point disposed at said distal end to affix said tubular member to an attached device.

32. The apparatus of claim 31 wherein said attached device includes a medical device.

33. The apparatus of claim 31 wherein said attached device is permanently affixed to said tubular member.

34. The apparatus of claim 31 wherein said attached device is temporarily affixed to said tubular member.

35. The apparatus of claim 11, further comprising a connector hub disposed at said proximal end.

36. The apparatus of claim 35 wherein said connector hub includes strain relief.

37. The apparatus of claim 11, further comprising an interface system having a tuning/matching circuit and a decoupling circuit, said interface system interposed between said detector coil and an MRI imaging system.

38. The apparatus of claim 11, wherein at least one of said exterior surface and said interior surface is coated with a lubricious material.

39. The apparatus of claim 38, wherein said lubricious material includes at least one of polyvinylpyrrolidone, polyacrylic acid, or silicone.

40. An apparatus for internally imaging using MRI comprising:
   a detector coil for internally imaging using MRI; and
   a trigger mechanism in communication with said detector coil;
   wherein activation of said trigger mechanism causes said detector coil to change from a collapsed state to an expanded state.

41. The apparatus of claim 40, wherein said trigger mechanism comprises a pull wire.

42. The apparatus of claim 40, wherein said detector coil in said collapsed state is dimensionally different from said detector coil in said expanded state.

43. A system for imaging using magnetic resonance imaging (MRI) comprising:
   a first detector coil for internally detecting magnetic resonance;
   a second detector coil for internally detecting magnetic resonance; and
   a controller for using said first detector coil in combination with said second detector coil for detecting magnetic resonance in an area to be imaged.

44. The system of claim 43, wherein said controller is a computer.

45. The system of claim 43, wherein said controller uses said first detector coil in parallel with said second detector coil.

46. The system of claim 43, wherein said controller can select to image using said first detector coil independently of said second detector coil.

47. The system of claim 43 further comprising a third detector coil externally detecting magnetic resonance.

48. The system of claim 43, wherein said controller creates a combined image from an image generated by said first detector coil and an image generated by said second detector coil.

49. A method for imaging using magnetic resonance imaging (MRI) comprising:
   placing a first and a second detector coil internal to a subject and adjacent to an area for imaging;
   generating magnetic resonance in said area; and
   moving said first detector coil relative to said second detector coil so that the coils in combination detect said magnetic resonance.

50. The method of claim 49 wherein the step of placing, at least one of said first detector coil and said second detector coil can detect said magnetic resonance.

51. The method of claim 49 wherein during the step of placing, magnetic resonance is generated.

* * * * *